United States Patent
Xiao et al.

(10) Patent No.: US 10,640,810 B2
(45) Date of Patent: May 5, 2020

(54) METHODS OF SPECIFICALLY LABELING NUCLEIC ACIDS USING CRISPR/CAS

(71) Applicants: Drexel University, Philadelphia, PA (US); The Wistar Institute of Anatomy and Biology, Philadelphia, PA (US); Temple University—of the Commonwealth System of Higher Education, Philadelphia, PA (US)

(72) Inventors: Ming Xiao, Huntingdon Valley, PA (US); Harold C. Riethman, Chesapeake, VA (US); Wenhui Hu, Cherry Hill, NJ (US); Jennifer McCaffrey, Collegeville, PA (US)

(73) Assignees: Drexel University, Philadelphia, PA (US); The Wistar Institute of Anatomy and Biology, Philadelphia, PA (US); Temple University, Philadelphia, PA (US)

( * ) Notice: Subject to any disclaimer, the term of this patent is extended or adjusted under 35 U.S.C. 154(b) by 2 days.

(21) Appl. No.: 15/787,319

(22) Filed: Oct. 18, 2017

(65) Prior Publication Data
US 2018/0105867 A1 Apr. 19, 2018

Related U.S. Application Data

(60) Provisional application No. 62/410,322, filed on Oct. 19, 2016.

(51) Int. Cl.
*C12Q 1/6806* (2018.01)
*G01N 1/30* (2006.01)
*G01N 21/64* (2006.01)

(52) U.S. Cl.
CPC .......... *C12Q 1/6806* (2013.01); *C12Y 301/00* (2013.01); *G01N 1/30* (2013.01); *G01N 21/6428* (2013.01); *G01N 2021/6439* (2013.01)

(58) Field of Classification Search
None
See application file for complete search history.

(56) References Cited

U.S. PATENT DOCUMENTS

2014/0356867 A1 12/2014 Peter et al.
2015/0344873 A1 12/2015 Xiao
2016/0168621 A1 6/2016 Xiao et al.

FOREIGN PATENT DOCUMENTS

WO WO2016028843 A2 2/2016
WO WO2016061523 4/2016
WO WO2016089920 A1 6/2016
WO WO2016123243 A1 8/2016
WO WO2018075648 4/2018

OTHER PUBLICATIONS

Anton et al., "Visualization of specific DNA sequences in living mouse embryonic stem cells with a programmable fluorescent CRISPR/Cas system" 5(2) Nucleus 163-172 (2014).*
International search report and written opinion issued on PCT/US2017/057201 dated Jan. 16, 2018.
Adey, A., et al. (Dec. 2014) "In vitro, long-range sequence information for de novo genome assembly via transposase contiguity." Genome Research 24(12): 2041-2049.
Britten, R. J. (Nov. 2010). "Transposable element insertions have strongly affected human evolution." Proceedings of the National Academy of Sciences of the United States of America 107(46): 19945-19948.
Burton, J. N., et al. (Nov. 2013) "Chromosome-scale scaffolding of de novo genome assemblies based on chromatin interactions." Nature Biotechnology 31(12): 1119-1125.
McCaffrey et al, (Oct. 2015) CRISPR-CAS9 D10A nickase target-specific fluorescent labeling of double strand DNA for whole genome mapping and structural variation analysis, Nucleic Acids Research, 44(2):e11.
Sriram, K. K., et al. (Apr. 2014). "Direct optical mapping of transcription factor binding sites on field-stretched lambda-DNA in nanofluidic devices." Nucleic Acids Res 42(10): e85.
Stong, N., et al. (Jun. 2014). "Subtelomeric CTCF and cohesin binding site organization using improved subtelomere assemblies and a novel annotation pipeline." Genome Res 24(6): 1039-1050.
Teague, B., et al. (Jun. 2010) "High-resolution human genome structure by single-molecule analysis." Proceedings of the National Academy of Sciences of the United States of America 107(24): 10848-10853.
Tegenfeldt, J. O., et al. (Jul. 2004). "From the Cover: the dynamics of genomic-length DNA molecules in 100-nm channels." Proc Natl Acad Sci U S A 101(30): 10979-10983.

(Continued)

*Primary Examiner* — Nancy J Leith
(74) *Attorney, Agent, or Firm* — Howson & Howson LLP; Colleen Schaller

(57) ABSTRACT

Provided herein are methods of detecting a target nucleic acid sequence. In one embodiment, the method includes contacting genomic DNA with a guide RNA having a portion complementary to the target sequence in the genomic DNA and with Cas9 nickase to produce a single-strand break in the genomic DNA at a specific location adjacent to the target sequence. The method further includes contacting the nicked DNA with a polymerase and fluorescently labeled nucleotide. The fluorescently labeled nucleotide is incorporated into the nicked DNA at the specific location and the target nucleic acid sequence is detected via fluorescent label.

20 Claims, 6 Drawing Sheets
Specification includes a Sequence Listing.

(56) References Cited

OTHER PUBLICATIONS

Carrington et al, CRISPR-STAT: an easy and reliable PCR-based method to evaluate target-specific sgRNA activity, Nuc Acids Res, Aug. 2015, 43(22):e157.
Chaisson, M. J. P., et al. (Nov. 2015) "Resolving the complexity of the human genome using single-molecule sequencing." Nature 517(7536): 608-611.
Chan, T. F., et al. (Sep. 2006). "A simple DNA stretching method for fluorescence imaging of single DNA molecules." Nucleic Acids Res 34(17): e113.
Chen et al, Dynamic Imaging of Genomic Loci in Living Human Cells by an Optimized CRISPR/Cas System, Cell, 155:1479-91 (Dec. 2013).
Chen et al, Expanding the CRISPR imaging toolset with *Staphylococcus aureus* Cas9 for simultaneous imaging of multiple genomic loci, Nuc Acids Res, Jan. 2016.
Chen et al, Mapping translocation breakpoints by next-generation sequencing, Genome Res. Jul. 2008; 18(7): 1143-1149.
Cohn, L. B., et al. (Jan. 2015). "HIV-1 integration landscape during latent and active infection." Cell 160(3): 420-432.
Das, S. K., et al. (Oct. 2010). "Single molecule linear analysis of DNA in nano-channel labeled with sequence specific fluorescent probes." Nucleic Acids Res 38(18): e177.
Voskoboynik, A., et al. (Jul. 2013) "The genome sequence of the colonial chordate, Botryllus schlosseri." Elife 2(e00569).
Deng et al, CASFISH: CRISPR/Cas9-mediated in situ labeling of genomic loci in fixed cells, PNAS, 112(38):11870-5 (Sep. 2015).
Desfarges, S. and A. Ciuffi (Jan. 2010). "Retroviral integration site selection." Viruses 2(1): 111-130.
Dumas, L. J., et al. (Sep. 2012). "DUF1220-Domain Copy Number Implicated in Human Brain-Size Pathology and Evolution." American Journal of Human Genetics 91(3): 444-454.
Gnerre, S., et al. (Jan. 2011) "High-quality draft assemblies of mammalian genomes from massively parallel sequence data." Proceedings of the National Academy of Sciences of the United States of America 108(4): 1513-1518.
Hastie, A. R., et al. (Apr. 2013). "Rapid Genome Mapping in Nanochannel Arrays for Highly Complete and Accurate De Novo Sequence Assembly of the Complex Aegilops tauschii Genome." Plos One 8(2).

Jing, J., et al. (Jul. 1998). "Automated high resolution optical mapping using arrayed, fluid-fixed DNA molecules." Proc Natl Acad Sci U S A 95(14): 8046-8051.
Jo, K., et al. (Feb. 2007). "A single-molecule barcoding system using nanoslits for DNA analysis." Proc Natl Acad Sci U S A 104(8): 2673-2678.
Kaper, F., et al. (Mar. 2013). "Whole-genome haplotyping by dilution, amplification, and sequencing." Proceedings of the National Academy of Sciences of the United States of America 110(14): 5552-5557.
Kaul, Z., et al. (Jan. 2012). "Five dysfunctional telomeres predict onset of senescence in human cells." Embo Reports 13(1): 52-59.
Kuleshov, V., et al. (Feb. 2014) "Whole-genome haplotyping using long reads and statistical methods." Nature Biotechnology 32(3): 261-266.
Lackner et al, A generic strategy for CRISPR-Cas9-mediated gene tagging, 6, Nature Comm, Dec. 2015.
Lam, E. T., et al. (Aug. 2012) "Genome mapping on nanochannel arrays for structural variation analysis and sequence assembly." Nature Biotechnology 30(8): 771-776.
Linardopoulou, E. V., et al. (Dec. 2007). "Human subtelomeric WASH genes encode a new subclass of the WASP family." PLoS Genet 3(12): e237).
Ma et al, Multicolor CRISPR labeling of chromosomal loci in human cells, PNAS, 112(10):3002-7 (Mar. 2015).
Marie, R., et al. (Mar. 2013). "Integrated view of genome structure and sequence of a single DNA molecule in a nanofluidic device." Proc Natl Acad Sci U S A 110(13): 4893-4898.
Noble, C., et al. (Apr. 2015). "A fast and scalable kymograph alignment algorithm for nanochannel-based optical DNA mappings." Plos One 10(4): e0121905.
Peters, B. A., et al. (Jul. 2012) "Accurate whole-genome sequencing and haplotyping from 10 to 20 human cells." Nature 487(7406): 190-195.
Qi, Z., et al. (Feb. 2015). "DNA sequence alignment by microhomology sampling during homologous recombination." Cell 160(5): 856-869.
Samad, A., et al. (Aug. 1995) "Optical Mapping—A novel, single-molecule approach to genomic analysis." Genome Research 5(1):1-4.
Schroder, A. R. W., et al. (Aug. 2002). "HIV-1 integration in the human genome favors active genes and local hotspots." Cell 110(4): 521-529.
Zou, Y., et al. (Aug. 2004) "Does a sentinel or a subset of short telomeres determine replicative senescence?" Molecular Biology of the Cell 15(8): 3709-3718.

\* cited by examiner

```
                        SEQUENCE LISTING

<160> NUMBER OF SEQ ID NOS: 16

<210> SEQ ID NO 1
<211> LENGTH: 20
<212> TYPE: RNA
<213> ORGANISM: Artificial Sequence
<220> FEATURE:
<223> OTHER INFORMATION: A sequence complementary to the 3'-5' strand of
      the homo sapiens telomere

<400> SEQUENCE: 1
uuaggguuag gguuaggguu                                                    20

<210> SEQ ID NO 2
<211> LENGTH: 20
<212> TYPE: RNA
<213> ORGANISM: Artificial Sequence
<220> FEATURE:
<223> OTHER INFORMATION: Sequence of gRNA for DUF1220.

<400> SEQUENCE: 2
aaguuccuuu uaugcauugg                                                    20

<210> SEQ ID NO 3
<211> LENGTH: 24
<212> TYPE: DNA
<213> ORGANISM: Artificial Sequence
<220> FEATURE:
<223> OTHER INFORMATION: Sequence of gRNA for HIV plasmid.

<400> SEQUENCE: 3
caccgcagga tatgtaactg acag                                               24

<210> SEQ ID NO 4
<211> LENGTH: 24
<212> TYPE: DNA
<213> ORGANISM: Artificial Sequence
<220> FEATURE:
<223> OTHER INFORMATION: Sequence of gRNA for HIV plasmid.

<400> SEQUENCE: 4
caccggccag atgagagaac caag                                               24

<210> SEQ ID NO 5
<211> LENGTH: 25
<212> TYPE: DNA
<213> ORGANISM: Artificial Sequence
<220> FEATURE:
<223> OTHER INFORMATION: Sequence of gRNA for HIV plasmid.

<400> SEQUENCE: 5
```
caccgagagt aagtctctca agcgg    25

<210> SEQ ID NO 6
<211> LENGTH: 20
<212> TYPE: RNA
<213> ORGANISM: Artificial Sequence
<220> FEATURE:
<223> OTHER INFORMATION: Sequence of gRNA for Chr1q telomere.

<400> SEQUENCE: 6
uuaggguuag gguuagggg uu    20

<210> SEQ ID NO 7
<211> LENGTH: 20
<212> TYPE: RNA
<213> ORGANISM: Artificial Sequence
<220> FEATURE:
<223> OTHER INFORMATION: Sequence of gRNA for Chr1q subtelomere.

<400> SEQUENCE: 7
ccccuguugc cagagccagu    20

<210> SEQ ID NO 8
<211> LENGTH: 20
<212> TYPE: RNA
<213> ORGANISM: Artificial Sequence
<220> FEATURE:
<223> OTHER INFORMATION: Sequence of gRNA for Chr1q subtelomere.

<400> SEQUENCE: 8
guauuuaguc agagggcuag    20

<210> SEQ ID NO 9
<211> LENGTH: 20
<212> TYPE: RNA
<213> ORGANISM: Artificial Sequence
<220> FEATURE:
<223> OTHER INFORMATION: Sequence of gRNA for Chr1q subtelomere.

<400> SEQUENCE: 9
auacaguagg auaaccgcaa    20

<210> SEQ ID NO 10
<211> LENGTH: 20
<212> TYPE: RNA
<213> ORGANISM: Artificial Sequence
<220> FEATURE:
<223> OTHER INFORMATION: Sequence of gRNA for Chr15q subtelomere.

<400> SEQUENCE: 10
accuugcuac cacgagagca    20

<210> SEQ ID NO 11
<211> LENGTH: 20
<212> TYPE: RNA
<213> ORGANISM: Artificial Sequence
<220> FEATURE:
<223> OTHER INFORMATION: Sequence of gRNA for Chr15q subtelomere.

<400> SEQUENCE: 11
uccauugguu uaauuaggaa    20

<210> SEQ ID NO 12
<211> LENGTH: 20
<212> TYPE: RNA

```
<213> ORGANISM: Artificial Sequence
<220> FEATURE:
<223> OTHER INFORMATION: Sequence of gRNA for Chr11q subtelomere.

<400> SEQUENCE: 12
gguccacccu acagaugugc                                                    20

<210> SEQ ID NO 13
<211> LENGTH: 20
<212> TYPE: RNA
<213> ORGANISM: Artificial Sequence
<220> FEATURE:
<223> OTHER INFORMATION: Sequence of gRNA for Chr11q subtelomere.

<400> SEQUENCE: 13
agaucagcag ccacgugugc                                                    20

<210> SEQ ID NO 14
<211> LENGTH: 20
<212> TYPE: RNA
<213> ORGANISM: Artificial Sequence
<220> FEATURE:
<223> OTHER INFORMATION: Sequence of gRNA for Chr12p subtelomere.

<400> SEQUENCE: 14
accuugcuac cacgagagca                                                    20

<210> SEQ ID NO 15
<211> LENGTH: 20
<212> TYPE: RNA
<213> ORGANISM: Artificial Sequence
<220> FEATURE:
<223> OTHER INFORMATION: Sequence of gRNA for Chr12p subtelomere.

<400> SEQUENCE: 15 uccaugguu uaauuaggaa                                                     20

<210> SEQ ID NO 16
<211> LENGTH: 20
<212> TYPE: RNA
<213> ORGANISM: Artificial Sequence
<220> FEATURE:
<223> OTHER INFORMATION: Sequence of gRNA for Alu.

<400> SEQUENCE: 16
uguaauccca gcacuuuggg                                                    20
```

METHODS OF SPECIFICALLY LABELING NUCLEIC ACIDS USING CRISPR/CAS

CROSS-REFERENCE TO RELATED APPLICATIONS

This application claims the benefit under 35 USC 119(e) of U.S. Provisional Patent Application No. 62/410,322, filed Oct. 19, 2016, which is incorporated by reference herein.

STATEMENT REGARDING FEDERALLY SPONSORED RESEARCH OR DEVELOPMENT

This invention was made with government support under R01 HG005946 and CA177395 awarded by National Institutes of Health. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "DRX_15-1773US_ST25.txt".

BACKGROUND OF THE INVENTION

Two of the major challenges in genome analysis are de novo genome sequence assembly based on 'short read' shotgun sequencing and structural variation analysis. Several approaches and combinations of different approaches have been attempted to meet these challenges. The most widely adopted strategy relies on deep sequencing of shotgun libraries and sequencing of mate-pair libraries, which increases the sequence contiguity of short-read sequencing (See, Siegel, A. F., et al. (2000) "Modeling the feasibility of whole genome shotgun sequencing using a pairwise end strategy." Genomics 68(3): 237-246). The paired sequencing approach includes conventional mate-pair libraries, labor-intensive fosmid or BAC clone libraries (See Gnerre, S., et al. (2011) "High-quality draft assemblies of mammalian genomes from massively parallel sequence data." Proceedings of the National Academy of Sciences of the United States of America 108(4): 1513-1518), Hi-C read-pairs for chromosome-scale scaffolding (See Burton, J. N., et al. (2013) "Chromosome-scale scaffolding of de novo genome assemblies based on chromatin interactions." Nature Biotechnology 31(12): 1119-1125) and transposase-mediated libraries (See Adey, A., et al. (2014) "In vitro, long-range sequence information for de novo genome assembly via transposase contiguity." Genome Research 24(12): 2041-2049). Another approach relies on the stochastic separation of corresponding genomic or polymerase chain reaction (PCR) fragments into physically distinct pools followed by subsequent fragmentation to generate shorter sequencing templates (See, Kaper, F., et al. (2013). "Whole-genome haplotyping by dilution, amplification, and sequencing." Proceedings of the National Academy of Sciences of the United States of America 110(14): 5552-5557; Kuleshov, V., et al. (2014) "Whole-genome haplotyping using long reads and statistical methods." Nature Biotechnology 32(3): 261-266; Peters, B. A., et al. (2012) "Accurate whole-genome sequencing and haplotyping from 10 to 20 human cells." Nature 487(7406): 190-195; and Voskoboynik, A., et al. (2013) "The genome sequence of the colonial chordate, *Botryllus schlosseri*." Elife 2(e00569)). With appropriate high-throughput reaction handling and barcoding, this strategy reduces the complexity, and thus can improve the quality, of assemblies. Longer-read sequencing technologies such as PacBio®'s SMRT and Oxford Nanopore sequencing promise to eventually further improve assembly contiguity. For example, SMRT sequencing has been successfully applied to closing some gaps and detecting some structural variations in the human reference genome (For example, See Chaisson, M. J. P., et al. (2015) "Resolving the complexity of the human genome using single-molecule sequencing." Nature 517(7536): 608-611). However, their high error rate, low throughput and high cost have thus far prevented widespread adoption.

None of the aforementioned approaches, however, adequately address the problems of long-range de novo assembly contiguity and validation, sequence mis-assembly in complex segmentally duplicated and repetitive regions, and structural variant detection and delineation. Whole genome mapping technologies have been developed for these purposes as complementary tools to provide scaffolds for genome assembly and structural variation analysis. Optical mapping, pioneered by David Schwartz and colleagues has been used to construct restriction maps for various genomes and has proven to be very useful in providing scaffolds for shotgun sequence assembly and detection of structural variations (See, Samad, A., et al. (1995) "Optical Mapping—A novel, single-molecule approach to genomic analysis." Genome Research 5(1): 1-4; and Teague, B., et al. (2010) "High-resolution human genome structure by single-molecule analysis." Proceedings of the National Academy of Sciences of the United States of America 107(24): 10848-10853). Furthermore, Ming Xiao and colleagues developed a highly-automated whole genome mapping in a nanochannel array (Hastie, A. R., et al. (2013). "Rapid Genome Mapping in Nanochannel Arrays for Highly Complete and Accurate De Novo Sequence Assembly of the Complex *Aegilops tauschii* Genome." Plos One 8(2); Lam, E. T., et al. (2012) "Genome mapping on nanochannel arrays for structural variation analysis and sequence assembly." Nature Biotechnology 30(8): 771-776 and US 2016/0168621 A1. Each of these documents is incorporated herein by reference.

The above-described genome mapping strategies are based on mapping the distribution of short (from 6 bp to 8 bp) sequence motifs across the genome. However, the distribution of the sequence motifs is uneven at different genomic regions. Often, there are no appropriate sequence motifs in repetitive genomic regions, which results in large segments of the genome that cannot be mapped (Feuk, L., et al. (2006). "Structural variation in the human genome." Nature Reviews Genetics 7(2): 85-97). Another challenge resides in detecting and typing structural variations or clinical diagnostics of specific structural variants. Target sequence-specific labeling of the structural variations is required to obtain accurate breaking points, but this cannot be achieved by sequence-motif mapping.

SUMMARY OF THE INVENTION

Provided herein are methods for sequence-specific labeling which is capable of targeting repetitive regions that often lack restriction site motif. In one aspect, methods of detecting a target nucleic acid sequence are provided. In one embodiment, the method includes contacting genomic DNA with a guide RNA having a portion complementary to the target sequence in the genomic DNA and with Cas9 nicking endonuclease (nickase) to produce a single-strand break (nick) in the genomic DNA at a specific location adjacent to the target sequence. The method further includes contacting the nicked DNA with a polymerase and fluorescently labeled nucleotide. The fluorescently labeled nucleotide is incorporated into the nicked DNA at the specific location and the target nucleic acid sequence is detected via fluorescent label.

In one embodiment, the method further includes contacting the genomic DNA with a second nicking endonuclease which is specific for a sequence motif in the genomic DNA thereby producing a second nick in the genomic DNA at the motif sequence. The nicked DNA is contacted with a polymerase and second fluorescently labeled nucleotide, wherein the second fluorescently labeled nucleotide is incorporated into the nicked DNA at the motif sequence location.

In another embodiment, the genomic DNA is contacted with a second nicking endonuclease which is specific for a sequence motif in the genomic DNA thereby producing a second nick in the genomic DNA at the motif sequence, wherein the first fluorescently labeled nucleotide is also incorporated into the nicked DNA at the motif specific location.

In another embodiment, the genomic DNA is contacted with multiple guide RNAs, each guide RNA having a portion complementary to a different target sequence in the genomic DNA, wherein each target nucleic acid sequence is detected via the same or different fluorescent label, thus providing a barcode of a portion of the genomic DNA.

Other aspects of the invention will be apparent from the description and examples below.

DETAILED DESCRIPTION OF THE INVENTION

The methods described herein used a modified CRISPR/Cas system. Clustered regularly interspaced short palindromic repeats (CRISPR) are segments of prokaryotic DNA containing short repetitions of base sequences. Each repetition is followed by short segments of "spacer DNA" from previous exposure to a bacteriophage virus or plasmid.

CRISPR associated proteins (Cas) use the CRISPR spacers to recognize and cut these exogenous genetic elements in a manner analogous to RNA interference in eukaryotic organisms.

Recently, a new genome editing tool based on a bacterial CRISPR-associated protein-9 nuclease (Cas9) from *Streptococcus pyogenes* has been developed for generating double strand DNA breaks in vivo. To achieve site-specific DNA recognition and cleavage, the protein Cas9 must form a complex with a guide RNA (gRNA) comprised of a crRNA and a trans-activating crRNA (tracrRNA), which is partially complementary to the crRNA. The HNH and RuvC-like nuclease domains of Cas9 cut both DNA strands, generating double-stranded breaks (DSBs) at sites defined by a 20-nucleotide seed sequence within an associated crRNA transcript. Mutations of both nuclease domains generate nuclease-deficient Cas9 (dCas9) that is still capable of binding to gRNA and moving to the target sequence, and has been used to visualize repetitive DNA sequences. Other mutant forms which lack just the RuvC-like nuclease domain activity, only nick the DNA strand complementary to its crRNA, are is characterized as Cas9 nickases (Cas9n). This type of mutant of Cas9 has been used with paired singled guide RNA (sgRNA) targeting opposite strands of the same locus to generate DSBs with great precision.

As described herein, the Cas9n-dependent nicking protocol is combined with motif-dependent nicking to fluorescently label specific sequences for whole genome mapping and other applications as described herein, through in vitro nick-labeling.

Figure 1A:
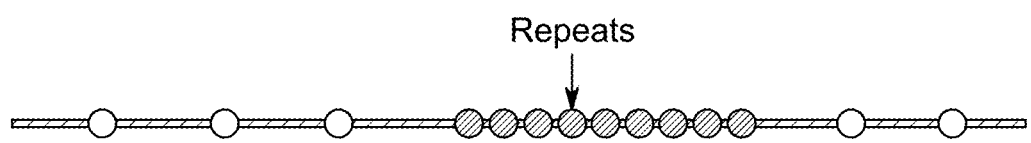
FIG. 1A is a schematic graph illustrating sequence motif fluorescent DNA labeling. The repetitive elements contain no recognition motifs for nicking enzymes (empty circles), and therefore this region is undetectable by conventional sequence-motif dependent nick labeling. However, this region can be mapped by the new Cas9n fluorescent nick-labeling method (circles filled with lines).
Figure 1B:
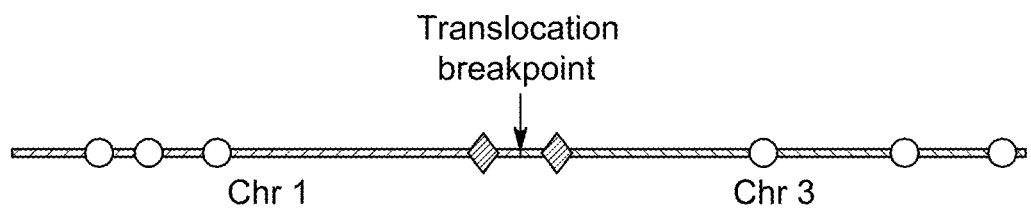
FIG. 1B is a schematic graph illustrating target sequence specific fluorescent DNA labeling. The Cas9n fluorescent nick-labeling system can identify translocations by designing gRNAs to target Cas9n D10A to nick specific sequences near the breakpoints (diamonds). These translocation breakpoint regions can then be precisely mapped by visualizing the targeted Cas9n fluorescent nick-labeling system-dependent signals relative to the conventional sequence motif-label-dependent bar codes generated on the breakpoint-adjacent large DNA segments (circles).

Such Cas9n fluorescent nick labeling based sequence-specific labeling methods can be used to target repetitive regions which often lack appropriate restriction site motifs. This method can also help to precisely map the breaking points of structural variations such as translocations, by designing guide RNAs (gRNAs) to recognize and direct labeling of sequences near these breakpoints prior to high throughput single molecule analysis (FIG. 1B). Novel combinations of conventional sequence motif mapping and target-specific mapping will unleash the full potential of nanochannel array-based genome mapping methods.

Nicking

As used herein a "nickase" is an enzyme (e.g., an endonuclease) that causes breaks in one strand of the nucleic acid sequence ("nick"). Double-strand DNA breaks (DSB) occur or arise when both strands of the DNA duplex are severed. A "nick", also known as single-strand DNA break (SSB), can stimulate gene correction without the problems of DSB repair because the uncut DNA strand acts as a template to permit healing without alteration of genetic material.

A Cas9 nickase (also called Cas9n or, alternatively, Cas9) is used in the methods herein. In one embodiment, the Cas9 nickase is Cas9 D10A. Cas9 H840A is another nickase useful in the methods described herein. In one embodiment, the Cas9 nickase is a mutant protein, which contacts the dsDNA and makes a nick of a single strand. The Cas9 nickase generates a single-strand DNA break at a specific location based on a guide RNA-defined target sequence, rather than a double-strand DNA break ("cut") produced by the wild type enzyme. As used herein, the term "Cas9" is sometimes used interchangeably with "Cas9 nickase" or "Cas9 D10A". The use of Cas9 nickase for targeting and labeling DNA has been described. See, e.g., WO 2016/028843, which is incorporated herein by reference.

It is contemplated that other nucleases engineered to create nicks can be utilized in place of, or in conjunction with, the Cas9 described herein. Such endonucleases include, without limitation, homing endonucleases (HE), meganucleases, Transcription activator-like effector nuclease (TALEN), Zinc finger nuclease (ZFN), prokaryotic Argonaute (pAgo), and BurrH-based nuclease (BuDN). Homing endonucleases (HE) are double stranded DNases that have large, asymmetric recognition sites (12-40 base pairs) and coding sequences that are extremely rare and usually embedded in either introns or inteins. Single base changes do not abolish cleavage by HE but reduce its efficiency to variable extents. As a result, the observed sequence specificity of HE is typically in the range of 10-12 base pairs.

Meganuclease are endodeoxyribonucleases characterized by a large recognition site (double-stranded DNA sequences of 12 to 40 base pairs), for example, I-SceI. Transcription activator-like effector nucleases (TALEN) are restriction enzymes that can be engineered to cut specific sequences of DNA. They are made by fusing a TAL effector DNA-binding domain to a DNA cleavage domain (a nuclease which cuts DNA strands). When combined with a nuclease, DNA can be cut at specific location. The restriction enzymes can be introduced into cells, for use in gene editing or for genome editing in situ.

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms and serve as a prominent tool in the field of genome editing.

Prokaryotic Argonaute (pAgo) is an endo-ribonuclease that uses a small RNA guide molecule to specifically target a complementary RNA transcript. Prokaryotic Argonautes are prokaryotic homologs of eukaryotic Argonaute proteins, which are key enzymes in RNA interference pathways. An Argonaute can bind and cleave a target nucleic acid by forming a complex with a designed nucleic acid-targeting nucleic acid. Cleavage can introduce double stranded breaks in the target nucleic acid. A nucleic acid can be repaired e.g. by endogenous non-homologous end joining (NHEJ) machinery. A piece of nucleic acid can be inserted. Engineering of non-genomic nucleic acid is also contemplated. Modifications of designed nucleic acid-targeting nucleic acids and Argonautes can introduce new functions to be used for genome engineering.

The method also includes contacting the genomic DNA with a motif-specific nicking endonuclease (also called "motif-specific nickase" or "motif-specific endonuclease") thereby producing a second nick in the genomic DNA at the motif sequence. As used herein a "motif" sequence refers to a short DNA sequence, which generally recurs in the genome. One of the major functions of motifs is indicating sequence-specific binding sites for proteins such as nucleases and transcription factors (TF).

The motif-specific nickase is used to nick the DNA at various locations where the motif is present. Such motif-specific endonucleases are known in the art and are characterized in that they only cut one strand ("nick") of the double stranded DNA, and are thus termed "nickases". In one embodiment, the motif-specific nickase is Nt.BspQI. In another embodiment, the nickase is selected from Nt. CviPII, Nt.AlwI, Nt.BsmAI, Nt.BstNBI, Nb.BsmI, Nb.BsrDI, Nb.BtsI, Nb.BbvCI and Nt.BbvCI. Other motif-specific nickases useful herein are contained in Table 1 below, with the motif sequence that they recognize. The appropriate nickase may be selected based on desired application and the portion of the DNA being surveyed.

TABLE 1

Nickases

| NICKASE | RECOGNITION SEQUENCE |
|---|---|
| Nt.AlwI | GGATC (4/none) |
| Nb.BbvCI | CCTCAGC (none/-2) |
| Nt.BbvCI | CCTCAGC (-5/none) |
| Nt.BhaIII | GAGTC (4/none) |
| Nb.Bpu10I | CCTNAGC (none/-2) |
| Nt.Bpu10I | CCTNAGC (-5/none) |
| Nt.Bpu10IB | CCTNAGC (-5/none) |
| Nb.BsaI | GGTCTC |
| Nt.BsaI | GGTCTC (1/none) |
| Nb.BsmI | GAATGC (none/-1) |
| Nb.BsmAI | GTCTC (none/5) |
| Nt.BsmAI | GTCTC (1/none) |
| Nt.BsmBI | CGTCTC (1/none) |
| Nt.BspD6I | GAGTC (4/none) |
| Nb.BspQI | GCTCTTC |
| Nt.BspQI | GCTCTTC (1/none) |
| Nb.BsrDI | GCAATG (none/0) |
| Nb.BssSI | CACGAG (none/-1) |
| Nt.Bst9I | GAGTC (4/none) |
| Nt.BstNBI | GAGTC (4/none) |
| Nt.BstSEI | GAGTC (4/none) |
| Nb.BtsI | GCAGTG (none/0) |
| Nb.BtsCI | GGATG |
| Nt.BtsCI | GGATG |
| Nt.CviPII | CCD (-3/none) |
| Nt.CviQII | RAG (-2/none) |
| Nt.CviQXI | RAG (-2/none) |
| V.Gel16401III | CGCG |
| Nt.MlyI | GAGTC (5/none) |
| Nb.Mva1269I | GAATGC (none/-1) |
| Nb.SapI | GCTCTTC |
| Nt.SapI | GCTCTTC |

In one embodiment of the method, the genomic DNA is contacted with a guide RNA having a portion complementary to a target sequence in the genomic DNA and with Cas9 nickase to produce a nick in the genomic DNA at a specific location adjacent to the target sequence. The nicked DNA is contacted with a polymerase and fluorescently labeled nucleotide, wherein the fluorescently labeled nucleotide is incorporated into the nicked DNA at the specific location. The method further includes contacting the genomic DNA with a motif-specific nicking endonuclease thereby producing a second nick in the genomic DNA at the motif sequence. The nicked DNA is contacted with a polymerase and second fluorescently labeled nucleotide of the same color or different color, wherein the second fluorescently labeled nucleotide is incorporated into the nicked DNA at the motif sequence location. In another embodiment, the DNA is contacted with the motif-specific nickase prior to contacting with the Cas9 nickase. In another embodiment, where the same fluorescently labeled nucleotide is used, the DNA is contacted with both nickases at about the same time.

As used herein, the term "guide RNA" may refer to the combination of a long, chemically synthesized trans-activating CRISPR RNA (tracrRNA) plus a chemically synthesized CRISPR RNA (crRNA), which is partially complementary to the gene target site of interest. The term "guide RNA" may also, in another embodiment, refer to an expressed single guide RNA (sgRNA) that consists of both the crRNA and tracrRNA as a single construct.

In one embodiment, a guide RNA has a portion which is complementary to the target sequence in the genomic DNA. The "seed sequence" is complementary to the target DNA sequence and is incorporated into the crRNA. The crRNA is used in conjunction with the universal tracrRNA. In one embodiment, the gRNA is created by pre-incubating the tracrRNA and crRNA prior to contacting with the Cas9 enzyme.

In one embodiment, the crRNA and/or tracrRNA is chemically synthesized. In another embodiment, the crRNA and/or tracrRNA is in vitro transcribed. In yet another embodiment, the crRNA and/or tracrRNA is vector encoded and recombinantly produced.

In one embodiment, the gRNA (either sgRNA or crRNA/tracrRNA) is pre-incubated with the Cas9 before contacting with the genomic DNA to form a complex. In another embodiment, the gRNA and Cas9 are contacted with the DNA at approximately the same time.

In another embodiment, the guide RNA is expressed as a single guide RNA (sgRNA). In one embodiment, the sgRNA is chemically synthesized. In another embodiment, the sgRNA is in vitro transcribed. In yet another embodiment, the sgRNA is vector encoded and recombinantly produced.

Fluorescent Labeling

In the methods described herein, the DNA nicks are repaired using nucleotides which are fluorescently labelled, in conjunction with a DNA polymerase. The fluorescently labelled nucleotide is separately selected for both the Cas9 nick labeling step and the motif-specific nickase labeling step. That is, the same, or different fluorescent labelled nucleotides can be used for the Cas9 nick labeling step and the motif-specific nickase labeling step. Fluorescent labeling is a process of incorporating a fluorescent tag to a molecule or in a system to visualize the fluorescent tag, also known as a label or probe. Fluorescent dyes are covalently bound to biomolecules such as nucleic acids or proteins so that they can be visualized by fluorescence imaging. Suitable fluorescently labeled nucleotides are known in the art and include, without limitation, Alexa Fluor® 555-aha-dCTP, Alexa Fluor® 555-aha-dUTP, Alexa Fluor® 647-aha-dCTP, Alexa Fluor® 647-aha-dUTP, ChromaTide® Alexa Fluor® 488-5-dUTP, ChromaTide® Alexa Fluor® 546-14-dUTP, ChromaTide® Alexa Fluor® 568-5-dUTP, ChromaTide® Alexa Fluor® 594-5-dUTP, ChromaTide® Fluorescein-12-dUTP, ChromaTide® Texas Red®-12-dUTP, Fluorescein-aha-dUTP, DY-776-dNTP, DY-751-dNTP, ATTO 740-dNTP, ATTO 700-dNTP, ATTO 680-dNTP, ATTO 665-dNTP, ATTO 655-dNTP, OYSTER-656-dNTP, Cy5-dNTP, ATTO 647N-dNTP, ATTO 633-dNTP, ATTO Rho14-dNTP, ATTO 620-dNTP, DY-480XL-dNTP, ATTO 594-dNTP, ATTO Rho13-dNTP, ATTO 590-dNTP, ATTO Rho101-dNTP, Texas Red-dNTP, ATTO Thio12-dNTP, ATTO Rho12-dNTP, 6-ROX-dNTP, ATTO Rho11-dNTP, ATTO 565-dNTP, ATTO 550-dNTP, 5/6-TAMRA-dNTP, Cy3-dNTP, ATTO Rho6G-dNTP, DY-485XL-dNTP, ATTO 532-dNTP, 6-JOE-dNTP, ATTO 495-dNTP, BDP-FL-dNTP, ATTO 488-dNTP, 6-FAM-dNTP, 5-FAM-dNTP, ATTO 465-dNTP, ATTO 425-dNTP, ATTO 390-dNTP and MANT-dNTP. Suitable fluorescently labeled nucleotides also include dideoxynucleotides (ddNTPs). Each of the listed labels used with dNTPs is suitable for use with ddNTPs (e.g., ATTO 488-ddNTP) and is intended to refer to either a dNTP or ddNTP. Methods for nick-labeling are known in the art, and are described herein. See, e.g., Rigby, P. W. J., et al. [1977] J. Mol. Biol. 113:237, which is incorporated herein by reference.

In one embodiment, the fluorescent label used in the Cas9 labeling and the motif-specific labeling are different. In this embodiment, removal of the free nucleotides is performed. This can be accomplished by dialysis or via enzyme. Such methods are known in the art and are described in the examples. In one embodiment, the free nucleotides are removed via dialysis. In another embodiment, the free nucleotides are removed via enzyme. Such enzymes include shrimp alkaline phosphatase and pyrrolidonyl peptidase.

The nicked DNA is labeled using a DNA polymerase. In one embodiment, the DNA polymerase has exonuclease activity. Such DNA polymerases include, without limitation, Taq DNA Polymerase, E. coli DNA Polymerase I and Bst DNA Polymerase. In one embodiment, the polymerase is Taq DNA polymerase.

In one embodiment, the labeled DNA is repaired with a DNA ligase.

In another embodiment, the method includes RNAse treatment after the Cas9-dependent nicking step. In yet another embodiment, the method includes protease treatment.

In one embodiment, the DNA backbone is stained. Suitable dyes are known in the art and include, without limitation, YOYO-1, YOYO-3, YO-PRO-1, TOTO-1, TO-PRO-1, TO-PRO-3, TO-PRO-5, POPO, BOBO, JOJO, LOLO, ethidium bromide (EB), propidium iodide (PI), Hoechst 33342, 4', 6-diamidino-2-phenylindole (DAPI), acridine orange, 7-AAD, LDS 751, hydroxystilbamidine, PicoGreen, OliGreen, RiboGreen, SYTOX Green/Blue/Orange, SYTO, and SYBR.

Visualizing DNA

In one embodiment, the genomic DNA is linearized and visualized after labeling. Methods of single DNA molecule fluorescence imaging are known in the art and include use of, e.g., nanochannels, nanopores or nanogaps.

In one embodiment, after the DNA is labelled using the methods described herein, the DNA is visualized. In one embodiment, the DNA labeling is visualized using a nanochannel, nanopore or nanogap. Visualizing DNA or optical mapping typically relies on sequence-specific DNA modifications at short target sites followed by imaging via Total Internal Reflection Fluorescence (TIRF) Microscopy (Chan, T. F., et al. (2006). "A simple DNA stretching method for fluorescence imaging of single DNA molecules." Nucleic Acids Res 34(17): e1113), super-resolution microscopy and other microscopies. These techniques can roughly be divided into three groups: stretching over a surface, stretching via confinement in nanochannels, or stretching via elongational flow in micro/nanochannels. See, e.g., Noble, C., et al. (2015). "A fast and scalable kymograph alignment algorithm for nanochannel-based optical DNA mappings." Plos One 10(4): e0121905); Chan, T. F., et al. (2006). "A simple DNA stretching method for fluorescence imaging of single DNA molecules." Nucleic Acids Res 34(17): e113; Jing, J., et al. (1998). "Automated high resolution optical mapping using arrayed, fluid-fixed DNA molecules." Proc Natl Acad Sci USA 95(14): 8046-8051, Das, S. K., et al. (2010). "Single molecule linear analysis of DNA in nanochannel labeled with sequence specific fluorescent probes." Nucleic Acids Res 38(18): e177.; and Marie, R., et al. (2013). "Integrated view of genome structure and sequence of a single DNA molecule in a nanofluidic device." Proc Natl Acad Sci USA 110(13): 4893-4898, each of which is incorporated herein by reference in its entirety.

Variants of flow stretching are implemented by attaching a large bead at the end of the DNA (Sriram, K. K., et al. (2014). "Direct optical mapping of transcription factor binding sites on field-stretched lambda-DNA in nanofluidic devices." Nucleic Acids Res 42(10): e85) or by a DNA molecular tethering in both or a single end by chemical bonds (Qi, Z., et al. (2015). "DNA sequence alignment by microhomology sampling during homologous recombination." Cell 160(5): 856-869), each of which is incorporated herein by reference in its entirety.

Nanopore and nanogap are also utilized for stretching, linearizing and imaging single DNA molecular. When a nanopore is immersed in a conducting fluid and a potential (voltage) is applied across it, an electric current due to conduction of ions through the nanopore can be observed. The amount of current is very sensitive to the size and shape of the nanopore. The capacitance, conductance and permittivity profiles of the Sub-10 nm nanogap electrodes are able to differentiate complementary, non-complementary and single mismatch target hybridization.

Elongation due to confinement in nanochannels can be performed by confining the DNA in one dimension by using a nanoslit or in two dimensions by using a nanoscale channel. See, e.g., Tegenfeldt, J. O., et al. (2004). "From the Cover: The dynamics of genomic-length DNA molecules in 100-nm channels." Proc Natl Acad Sci USA 101(30): 10979-10983; and Lam, E. T., et al. (2012). "Genome mapping on nanochannel arrays for structural variation analysis and sequence assembly." Nat Biotechnol 30(8): 771-776; Jo, K., et al. (2007). "A single-molecule barcoding system using nanoslits for DNA analysis." Proc Natl Acad Sci USA 104(8): 2673-2678 and Kounovsky-Shafer, K. L., et al. (2013). "Presentation of large DNA molecules for analysis as nanoconfined dumbbells." Macromolecules 46(20): 8356-8368, each of which is incorporated herein by reference.

Methods of using nanochannel arrays are known in the art. See, e.g., Lam et al, cited above). Briefly, a nanofluidic chip is provided that contains nanochannels that keep long DNA molecules in a consistent, uniformly elongated state. Fluorescently labeled DNA molecules are drawn into the nanochannels, held still and imaged automatically on the multicolor Irys® instrument. After imaging, additional sets of DNA molecules are streamed into the nanochannels for imaging. This process is repeated many times until the DNA is depleted or the nanochannels are rendered unusable as a result of clogging.

The nanofluidic chip contains three sets of nanochannels, each consisting of ~4,000 channels that are 0.4 mm in length and 45 nm in diameter. Using 193-nm lithography in a nanofabrication process on the surface of a silicon substrate, nanochannel array chips are produced with precise diameters. DNA molecules in the 45-mm nanochannels cannot fold back on themselves and are forced by physical confinement to be in an elongated, linearized state.

As long DNA molecules in solution exist as coiled balls, a gradient region consisting of pillars and wider channels is placed in front of the nanochannels to allow the DNA molecules to uncoil as they flow toward the array. In this region, the physical confinement is sufficiently dense that the molecules are forced to interact with the pillars, yet sufficiently sparse that the DNA is free to uncoil. Once uncoiled, the DNA can then be efficiently flowed into the array in a linear manner, and visualized fluorescently.

As used herein, a "barcode" refers to a pattern of fluorescent labeling that is specific to a particular chromosome or portion of genomic DNA. For example, the specific pattern of fluorescence of the motif nick-labeling can identify the specific chromosome or portion of DNA being visualized. Alternatively, the pattern of nick labeling of both the motif-specific nick labeling and Cas9-dependent nick-labeling can be used to identity the specific chromosome or portion of DNA being visualized. Such barcodes are useful in the embodiment of the method in which the labeling is used to help assemble sequencing reads, e.g., for de novo sequencing, or to determine the location of integration of a viral sequence in the genome.

Telomere repeats are immediately distal to subtelomeric repeat elements (SREs) which are approximately 80% of the most distal 150 kb of human subtelomeres. Long SRE regions of about 150 kb have been identified in some alleles of various telomeres, whereas 7 telomeres have minimal or no SRE content. Read lengths of greater than 50 kb are required for assembling these regions using single-molecule sequencing, which is beyond the capability of current technology. Furthermore, the telomere repeat sequence (TTAGGG)n sequence lacks motif nicking sites recognized by currently available nicking endonucleases and therefore cannot be labeled with sequence-motif based methods.

Figure 4A:
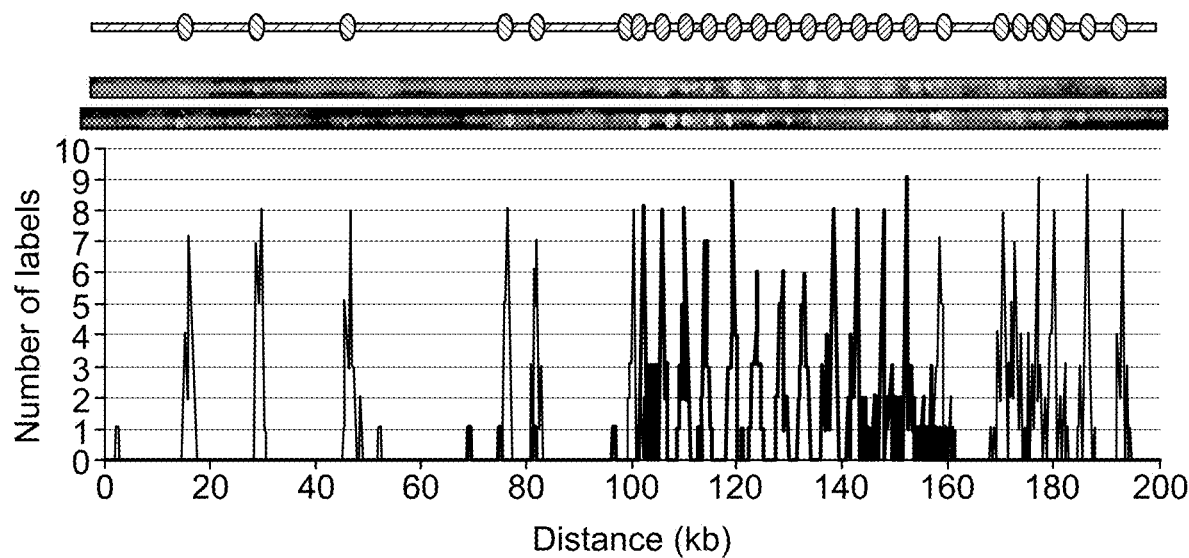
FIG. 4A is a graph showing that the Cas9n fluorescent nick-labeling method was used to label the repetitive sequences of the DUF1220 triplet (circles filled with forward slashes). These molecules were then labeled with the conventional sequence motif labeling method with Nt.BspQI (circles filled with backslashes). The expected labeling pattern and distances between labels is shown above corresponding fluorescent microscopy images. The histogram of the labels is shown below the molecules. The red peaks represent the DUF gRNA labels and the green the Nt.BspQI labeling sites. A total of 43 molecules were evaluated for the labeling efficiency.
Figure 4B:
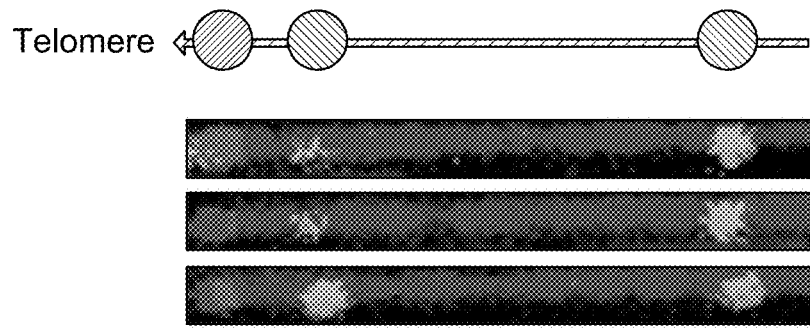
FIG. 4B shows a graph illustrating that the Cas9n fluorescent nick-labeling method was used to label the repetitive telomere sequences at the left end of these telomere-terminal DNA fragments. A gRNA targeting the repetitive telomere sequence $(TTAGGG)_n$, correctly labeled the telomere region on the left end of this telomere-terminal 1q DNA fragment (circle filled with forward slashes). The sequence-motif labeling method with Nt.BspQI was performed after Cas9n/gRNA system labeling of telomeres, and is displayed with circle filled with backslashes.

As described herein, the CRISPR-Cas9 nick-labeling technology was combined with the nickase based nick-labeling procedure, to label telomeric repeats and subtelomeric regions separately. CRISPR-Cas9 labeling in conjunction with a global nickase enzyme motif-dependent labeling method allows for accurate telomere length measurement of each chromosome arm (FIG. 4B).

In the examples below, a mutant form of Cas9, termed Cas9 D10A, which is catalytically modified, was used with a telomere targeting gRNA to nick-label the telomeric repeats. The labeled DNA molecules were linearized in nanochannels and optically imaged. The labels from the enzyme motif-dependent labeling step were mapped to a reference to identify the chromosomal location of the corresponding Cas9 D10A labeled telomere. The intensity of the telomeric labeling was used and converted into base pairs to calculate the telomere length. This method was developed as a two-color and three-color approach, as described herein.

In one aspect, a method of detecting the length of an individual telomere is provided. As noted above, several embodiments are provided which utilize different schemes to produce different "barcodes" for identification the specific chromosome being identified. In one embodiment of the method, the first 20 nucleotides of the gRNA are complementary to the 3' to 5' telomere repeat region which is followed immediately by the protospacer adjacent motif (PAM) NGG.

In one embodiment, sometimes called the "3-color" method, the method includes contacting genomic DNA with a guide RNA having a portion complementary to the telomere repeat sequence in the genomic DNA and with a Cas9 nickase to produce a single-strand break ("nick") in the genomic DNA at the telomere repeat sequence. The method further includes contacting the nicked DNA with a polymerase and fluorescently labeled nucleotide, wherein the fluorescently labeled nucleotide is incorporated into the nicked DNA at the telomere repeat sequence. The method further includes contacting the genomic DNA with a second nicking endonuclease which is specific for a sequence motif ("a motif-specific nickase") in the genomic DNA thereby producing a second nick in the genomic DNA at the motif sequence. In one embodiment, the nick is made at the motif sequence in more than one location in the genome, e.g., throughout the genome. The nicked DNA is contacted with a polymerase and second fluorescently labeled nucleotide of different color, wherein the second fluorescently labeled nucleotide is incorporated into the nicked DNA at the motif sequence location. The length of the telomere is detected by measuring the fluorescence of first fluorescently labeled nucleotide at the telomere repeat location. The fluorescently labeled motif sequences are used as a barcode to identify the chromosome.

Methods

For each of the methods described herein, it is intended that the Cas9 nick-labeling may be performed before or after the motif-endonuclease nick labeling. Where multiple gRNAs are used in conjunction with Cas9 (e.g., for telomeric and subtelomeric sequences or multiple repeated sequences), these steps may be performed together or separate, with either step coming first.

In one embodiment, the method is useful in visualizing telomeres and determining the length thereof. Thus, in one embodiment, a guide RNA has a portion which is complementary to the telomere repeat sequence in the genomic DNA. There are 92 telomeres in a diploid human cell ranging between 0.5 kb and 20 kb, which are made up of the telomere repeat sequence (TTAGGG)n. In one embodiment, the seed sequence of 20 nucleotides complementary to the 3'-5' strand of the telomere (UUAGGGUUAGGGUUAGGGUU—SEQ ID NO: 1) is incorporated into the crRNA. Other appropriate seed sequences based on the telomere repeat sequence can be designed by the person of skill in the art. The crRNA is used in conjunction with the universal tracrRNA. In one embodiment, the telomere gRNA is created by pre-incubating the tracrRNA and crRNA prior to contacting with the Cas9 enzyme. In one embodiment, the crRNA and/or tracrRNA is chemically synthesized. In another embodiment, the crRNA and/or tracrRNA is in vitro transcribed. In yet another embodiment, the crRNA and/or tracrRNA is vector encoded and recombinantly produced.

In one embodiment, the gRNA (either sgRNA or crRNA/tracrRNA) is pre-incubated with the Cas9 before contacting with the genomic DNA to form a complex. In another embodiment, the gRNA and Cas9 are contacted with the DNA at approximately the same time.

In another embodiment, the guide RNA is expressed as a single guide RNA (sgRNA). In one embodiment, the sgRNA is chemically synthesized. In another embodiment, the sgRNA is in vitro transcribed. In yet another embodiment, the sgRNA is vector encoded and recombinantly produced.

In another embodiment, sometimes called the "two-color" method, the genomic DNA is contacted with a guide RNA having a portion complementary to the telomere repeat sequence in the genomic DNA, and with a Cas9 nickase to produce a single-strand break in the genomic DNA at the telomere repeat sequence. The genomic DNA is also contacted with a second nicking endonuclease which is specific for a sequence motif in the genomic DNA, thereby producing a second nick in the genomic DNA at the motif sequence. The nicked DNA is contacted with a polymerase and fluorescently labeled nucleotide, wherein the fluorescently labeled nucleotide is incorporated into the nicked DNA at the telomere repeat sequence and at the motif sequence. The length of the telomere is detected by measuring the fluorescence of first fluorescently labeled nucleotide at the telomere repeat location and the fluorescently labeled motif sequences are used as a barcode to identify the chromosome. In this embodiment, the same fluorescent label is used to mark the motif sequences and the telomere sequences. In one embodiment, the telomere repeat sequence, the motif sequence, or both is present in more than one location in the genomic DNA.

In another embodiment, as an alternative, or in addition to, the motif-specific nickase, one or more additional guide RNAs are provided, which are complementary to one or more sequences in the genomic DNA other than the telomeric sequences. These gRNAs in combination with the Cas9 nickase can be used in a similar way to the motif-specific nickase to create a "barcode" to identify the chromosome. In one embodiment, the additional sequence is a sequence in the subtelomere region of the DNA. In another embodiment, multiple guide RNAs are provided to target multiple subtelomeric sequences. In one embodiment, the telomere repeat sequence, the subtelomeric sequence, or both is present in more than one location in the genomic DNA.

In one embodiment, the genomic DNA is contacted with a second guide RNA having a portion complementary to a sequence in the subtelomeric region of the genomic DNA and with Cas9 nickase to produce a single-strand break in the genomic DNA at the subtelomeric sequence. In one embodiment, the nicked DNA is contacted with a polymerase and second fluorescently labeled nucleotide, of a different color, wherein the second fluorescently labeled nucleotide is incorporated into the nicked DNA at the subtelomeric sequence location. The length of the telomere is detected by measuring the fluorescence of first fluorescently labeled nucleotide at the telomere repeat location, and the second fluorescently labeled subtelomeric sequence is used as a barcode to identify the chromosome.

In one embodiment, the second guide RNA comprises multiple guide RNAs, each guide RNA having a portion complementary to a different target sequence in the subtelomeric region of the DNA, wherein each subtelomeric sequence is detected via fluorescent label, thus providing a barcode of a portion of the genomic DNA.

In another embodiment, the DNA is nicked with both telomeric-directed Cas9 nickase and the subtelomeric-directed Cas9 nickase, and the same fluorescently labeled nucleotide is incorporated into the nicked DNA at the telomere repeat sequence and at the subtelomeric sequence. The length of the telomere is detected by measuring the fluorescence of the fluorescently labeled nucleotide at the telomere repeat location, and the fluorescently labeled subtelomeric sequence is used as a barcode to identify the chromosome.

As discussed herein, two labeling schemes for identifying genomic sequences are described, i.e., the so-called two-color and three-color methods. In both schemes, the same gRNA may be used to nick-label the first genomic sequence, and the remaining genomic DNA is globally nick-labeled using an endonuclease which is specific for a sequence motif in the DNA. Such motif-specific endonucleases are known in the art and are characterized in that they only cut one strand ("nick") of the double stranded DNA, and are thus termed "nickases". In one embodiment, the motif-specific nickase is Nt.BspQI. In another embodiment, the nickase is selected from Nt.CviPII, Nt.AlwI, Nt.BsmAI, Nt.BstNBI, Nb.BsmI, Nb.BsrDI, Nb.BtsI, Nb.BbvCI and Nt.BbvCI. Other motif-specific nickases useful herein are contained in Table 1 above.

In one embodiment, when two differently labeled fluorescent nucleotides are used, the unused nucleotides from the first nick labeling step are removed prior to the second nick labeling step.

In one embodiment, sometimes referred to as the "two-color" scheme, the Cas9n and Nt.BspQI are incubated with the human genomic DNA and simultaneously nick their respective regions. In the examples below, all of these nicks were labeled with green fluorescently labeled nucleotides using Taq DNA polymerase.

In the three color scheme, as described in the examples below, the Nt.BspQI was first incubated with the human genomic DNA and nicks the CGTCTTC motif. These nicks were labeled with green fluorescently labeled nucleotides using Taq DNA polymerase. After removing unused green fluorescent nucleotides with Shrimp Alkaline Phosphatase (SAP), the labeled DNA molecules were nicked with Cas9n and labeled with red fluorescently labeled nucleotides again using Taq DNA polymerase. The labeled DNA molecules were linearized in the nanochannels and optically imaged. De novo assembly was performed using the unique Nt.BspQI patterns referenced to hg38 and individual DNA molecules assembled are used for calculating the telomere length. This allowed for the identification of the chromosome arms with the corresponding telomere.

In one embodiment, the length of the telomere is detected by imaging the labeled telomere. In one embodiment, the contour of telomeric labeling is used to calculate telomere length. In another embodiment, the intensity of telomeric labeling is used to calculate telomere length. When viewed in a DNA imaging system, the longer the telomere, the more pixels it occupies. However, the ends of DNA molecules tend to fold back on to themselves which affects the length measurements. More importantly, due to photon scattering, even with single point emitter, several pixels collected photons. Thus, use of the contour method is less desirable for a telomere length less than 1 kb. This was observed with the telomeric labeling of the 8q fosmid with 800 bp of telomeric repeats occupying the same amount of pixels as a single fluorophore. Thus, for smaller telomeres, the total intensity of the telomere labels is a desirable method of measurement.

In one embodiment, to calculate the length of the telomere, the intensity of fluorescence is compared to a standard. For example, DNA which incorporates telomeres of known length can be included, visualized concurrently with the telomeres of unknown size, and the values compared. In another embodiment, the measurement is compared to a standard curve. Such values may be pre-existing based on prior data, or performed concurrently with the method. In another embodiment, background fluorescence is removed prior to calculation.

A decrease in the telomere length with later population doublings is detected because during each cell division telomeres become progressively shorter. It has been shown that a population of extremely short telomeres exists in human telomerase-positive human cancer cells and transformed fibroblast cells lacking tumor suppressor pathways. In fibroblasts with functional tumor suppressor pathways with or without telomerase these extremely short telomeres are rare.

Thus, in one aspect, a method of identifying a cancer cell is provided. The method includes detecting the length of the telomeres in the cell, or a portion thereof, using a method as described herein. The method further includes comparing the length of the telomeres to the length of telomeres to a standard. Such standards include a cancer cell, a healthy cell, an aging cell and a stem cell. In one embodiment, when one or more telomere is about 100 bp or more shorter as compared to a healthy cell, the cell is determined to be a cancer cell. In one embodiment, the method of identifying a cancer includes measuring the length of chromosome 8q.

The term "cancer" as used herein means any disease, condition, trait, genotype or phenotype characterized by unregulated cell growth or replication as is known in the art. A "cancer cell" is cell that divides and reproduces abnormally with uncontrolled growth. This cell can break away from the site of its origin (e.g., a tumor) and travel to other parts of the body and set up another site (e.g., another tumor), in a process referred to as metastasis. A "tumor" is an abnormal mass of tissue that results from excessive cell division that is uncontrolled and progressive, and is also referred to as a neoplasm. Tumors can be either benign (not cancerous) or malignant. The methods described herein are useful for the treatment of cancer and tumor cells, i.e., both malignant and benign tumors, so long as the cells to be treated have mitochondrial localization of the chaperones as described herein. In various embodiments of the methods and compositions described herein, the cancer can include, without limitation, breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, acute and chronic lymphocytic and myelocytic leukemia, myeloma, Hodgkin's and non-Hodgkin's lymphoma, and multidrug resistant cancer. In one embodiment, the cancer is a drug resistant cancer.

In one embodiment, the methods described herein are used to enable mapping of the genome, or a portion thereof. In this embodiment, the gRNA is directed to a region which is repeated throughout the genome, or a portion thereof. The Cas9 is then used to nick-label these sequences in combination with a fluorescently labeled nucleotide and polymerase. This Cas9 nick-labeling is, in one embodiment, used in conjunction with motif nick-labeling to enable enhanced nanochannel array-based genome mapping.

Most resequencing projects rely on mapping the sequencing data to the reference sequence to identify variants of interest. When whole-genome assembly is attempted, paired-end sequencing of long DNA fragments provides scaffolds for assembly. As cloning of large DNA fragments is difficult, small-insert libraries of varying sizes may be prepared for paired-end sequencing, thus limiting the resolution of haplotypes and increasing the complexity, time and cost of the sequencing project. In addition, complex genomic loci, contain highly repetitive sequences and are particularly difficult to assemble. The methods described herein aid in de novo sequence assembly.

In one embodiment, a method of detecting a target nucleic acid sequence is provided. The method includes contacting genomic DNA with a guide RNA having a portion complementary to the target sequence in the genomic DNA and with Cas9 nickase to produce a single-strand break in the genomic DNA at a specific location adjacent to the target sequence. The method further includes contacting the nicked DNA with a polymerase and fluorescently labeled nucleotide, wherein the fluorescently labeled nucleotide is incorporated into the nicked DNA at the specific location. The target nucleic acid sequence is detected via fluorescent label.

In one embodiment, the guide RNA is directed to a sequence which is found in more than one location of the genome (a "repeated seqeuence"). In one embodiment, the guide RNA is directed to a SINE sequence. Short interspersed elements (SINEs) are highly repetitive sequences that retrotranspose into eukaryotic DNA through intermediates transcribed by RNA polymerase III (pol III). In many species, SINEs are a ubiquitously dispersed feature of the whole genome, often constituting a significant (~10%) mass fraction of total DNA. SINEs cause mutations both by their retrotransposition within genes and by unequal recombination, and are widely considered to be examples of 'selfish' or 'parasitic' DNA. In one embodiment, the gRNA is directed to the Alu element. Alu sequences, with about one million copies, are the most abundant retroelements in humans, and account for up 10% of the human genome. These SINE sequences, exclusively found in primate genomes, have been particularly active in the human lineage even after human-chimpanzee divergence, where they are theorized to have contributed to some of the human-specific characteristics such as brain size (Britten, R. J. (2010). "Transposable element insertions have strongly affected human evolution." Proceedings of the National Academy of Sciences of the United States of America 107(46): 19945-19948). In one embodiment, the gRNA sequence is directed to target a subset of the Alu sites. Other SINE sequences are known in the art and can be targeted using the methods described herein, depending on the subject genome being investigated, copy number, etc. A list of SINE sequences which can be targeted using the methods of the invention include those found in Table 2 below. Such sequences can be accessed at sines.eimb.ru/, which is incorporated herein by reference.

In another embodiment, the gRNA is directed to the DUF1220 protein domain. Genome sequences encoding DUF1220 protein domains have undergone an exceptional human lineage specific (HLS) increase in copy number, which was implicated in human brain size, pathology and evolution (See, Dumas, L. J., et al. (2012). "DUF1220-Domain Copy Number Implicated in Human Brain-Size Pathology and Evolution." American Journal of Human Genetics 91(3): 444-454).

In one embodiment, the method includes the use of gRNAs to more than one repeated sequence. For example, one gRNA may be directed to the DUF1220 element and a second gRNA may be directed to the Alu element.

In another embodiment, the use of the Cas9 nick labeling of repeated sequences is used in combination with motif-specific nick labeling (e.g., thru motif-specific endonucleases).

In another aspect, the methods described herein are used to target viral sequences which have been incorporated into a host genome. For example, HIV-1 integrates into the human genome at different locations (See, Schroder, A. R. W., et al. (2002). "HIV-1 integration in the human genome favors active genes and local hotspots." Cell 110(4): 521-529), each of which may be identifiable directly through an appropriate integration site labeling and global genome mapping strategy. Identification of such sites in HIV-1 latent cells is essential for understanding the molecular and epigenetic mechanisms underlying HIV-1 latency (See, Cohn, L. B., et al. (2015). "HIV-1 integration landscape during latent and active infection." Cell 160(3): 420-432).

Similarly, this sequence-specific mapping approach is used to identify lentivirus random integration sites in the host cells, which may disrupt both endogenous gene expression and vector gene expression patterns (See, Desfarges, S. and A. Ciuffi (2010). "Retroviral integration site selection." Viruses 2(1): 111-130).

As discussed in the Examples below, multiple sgRNAs were designed and tested to target HIV-1 structural region (Gag, Pol, Env) to determine the most effective gRNA that labels the HIV-1 genome. In one embodiment, the gRNA targets a structural region of the viral genome. In another embodiment, multiple gRNAs are used which target different regions of the viral genome. Other viruses which may be targeted include, without limitation, HIV, lentivirus, HPV, HSV, and HBV.

In another embodiment, the methods described herein are used to identify translocation breakpoint regions by designing gRNAs to target Cas9 nickase to nick specific sequences near the breakpoints (FIG. 1B). These translocation breakpoint regions can then be precisely mapped by visualizing the targeted Cas9n fluorescent nick-labeling system-dependent signals relative to the conventional sequence motif-label-dependent bar codes generated on the breakpoint-adjacent large DNA segments (light grey circles). Methods of determining the position of the breakpoint are known in the art and include maximum likelihood estimation. See, e.g., Chen et al, Mapping translocation breakpoints by next-generation sequencing, Genome Res. 2008 July; 18(7): 1143-1149, which is incorporated herein by reference. In one embodiment, the gRNAs are directed to specific sequences near the breakpoint locus.

The methods described herein can be modified to target any desirable genomic sequence. In such embodiments, the first set of gRNA together with Cas9 is designed to be complementary to, and target, any genomic sequence to generate a nick. The second set of gRNA-Cas9 complexes or nicking endonuclease can target any other desirable different genomic sequences than first set of gRNAs.

As used herein, the terms "complementary", "complementarity" and "complement" have the same meaning as commonly used. Complementarity is a property shared between two nucleic acid sequences, such that when they are aligned antiparallel to each other, the nucleotide bases at each position will be complementary.

Technical and scientific terms used herein have the same meaning as commonly understood by one of ordinary skill in the art to which this invention

TABLE 2

| SINE Table—FIG. 6 | | | | |
|---|---|---|---|---|
| SINE Σ: 213 (100%) | Length (w/o tail) | Taxon | Distribution | Copy number |
| Mon1 | 270 | Mammalia | monotremes | $2 \times 10^6$ (platypus) |
| Alu | 282 | Mammalia | primates | $1.1 \times 10^6$ (human) $1.5 \times 10^5$ (galago) |
| CYN-II | 154 | Mammalia | flying lemur (*Cynocephalus*) | $1 \times 10^6$ (with CYN-I & CYN-III) |
| CYN-III | 203 | Mammalia | flying lemur (*Cynocephalus*) | $1 \times 10^6$ (with CYN-I & CYN-II) |
| PRE-1 | 246 | Mammalia | pigs and peccaries | $10^6$ (pig) |
| CYN-I (t-SINE) | 79 | Mammalia | flying lemur (*Cynocephalus*) | $1 \times 10^6$ (with CYN-II & CYN-III) |
| AfroSINE (AfroSINEn) | 230 | Mammalia | afrotherians | $8 \times 10^5$ |
| AfroLA (AFRO_LA, PSINE1) | 158 | Mammalia | elephants and mammoths (Proboscidea) | $7 \times 10^5$ (mammoth) |
| Lm1 (SGRP1) | 200 | Insecta | *Locusta, Schistocerca* & *Chorthippus* | $6 \times 10^5$ (locust) |
| C (CSINEn) | 325 | Mammalia | Lagomorpha | $5.4 \times 10^5$ |
| Mar1 (SINE1_MD) | 246 | Mammalia | marsupials (Metatheria) | $5 \times 10^5$ (opossum) |
| Cry (pol III/SINE, Hirt) | 200 | Reptilia | Cryptodira (straightneck turtles) | $5 \times 10^5$ |
| DANA | 370 | Actinopterygii | zebrafish (*Danio*) | $4.5 \times 10^5$ |
| Ther-1 (MIR) | 252 | Vertebrata | mammals, birds & reptiles | $4 \times 10^5$ (human) $1 \times 10^5$ (mouse, rat) |
| B4 (RSINE2, ID_B1) | 278 | Mammalia | different rodent families | $4 \times 10^5$ (mouse) $3.6 \times 10^5$ (rat) |
| Xt-1 (MIR_Xt) | 208 | Amphibia | *Xenopus tropicalis* | $4 \times 10^5$ |
| ERE-B (ERE-2x, ERE-3x) | 235 ~176 | Mammalia | horse (*Equus caballus*) | $3.8 \times 10^5$ |

TABLE 2-continued

SINE Table—FIG. 6

| SINE Σ: 213 (100%) | Length (w/o tail) | Taxon | Distribution | Copy number |
|---|---|---|---|---|
| B2 (B2s, B2l, B3, SINEB2) | 185 | Mammalia | Muridae, Cricetidae, Spalacidae & Rhizomiidae | $3.5 \times 10^5$ |
| SINE type II (GarnAlu) | 260 | Mammalia | bush babies and lorises (Lorisiformes) | $3 \times 10^5$ |
| Lun1 | 291 | Sarcopterygii | lungfish (*Lepidosiren paradoxa*) | $3 \times 10^5$ |
| Opo-1 (SINE-1_MD, SINE-2_MD) | 193 | Mammalia | American marsupials | $2.8 \times 10^5$ |
| TUB (TUB1, TUB2, TUB3, TUB4) | 131 | Mammalia | tree shrews (Scandentia) | $2.5 \times 10^5$ |
| UnaSINE1 | 208 | Actinopterygii | eel (*Anguilla japonica*) | $2.5 \times 10^5$ |
| Ped-2 | 185 | Mammalia | springhare (*Pedetes capensis*) | $2.5 \times 10^5$ |
| DAS-III | 387 | Mammalia | nine-banded armadillo (*Dasypus novemcinctus*) | $2.2 \times 10^5$ |
| Tu type III (TUBE1, TUS) | 242 | Mammalia | tree shrews (Scandentia) | $2 \times 10^5$ |
| Bov-tA (Bov-tAn) | 204 | Mammalia | Bovidae (cattle, goats & sheep) | $2 \times 10^5$ |
| CAN (SINEC*, MVB2) | 160 | Mammalia | Carnivora | $2 \times 10^5$ |
| SINE type III (Garnel 1) | 78 | Mammalia | bush babies and lorises (Lorisiformes) | $2 \times 10^5$ |
| SS-1 (SINE1_SS, SUSINE2) | 121 | Mammalia | pig (*Sus scrofa*) | $1.9 \times 10^5$ |
| ID-Spe (STRID2, STRID3, STRID4) | 126 | Mammalia | Sciuromorpha | $1.9 \times 10^5$ |
| Sepioth1 | 292 | Cephalopoda | Sepioteuthinae & Loliginidae | $1.8 \times 10^5$ |
| Sepia | 312 | Cephalopoda | cuttlefish (Sepiida) | $1.7 \times 10^5$ |
| Bm1 | 430 | Insecta | silkworm (*Bombyx mori*) | $1.5 \times 10^5$ |
| Sauria (Squam1, ACA, AFE, POM, VIN) | 350 | Reptilia | scaled reptiles (Squamata) | $1.3 \times 10^5$ |
| B1-dID (STRIDE*) | 200 | Mammalia | Gliridae, Sciuridae & Aplodontidae | $1.1 \times 10^5$ (dormouse) $4.5 \times 10^4$ (squirrel) $2.8 \times 10^4$ (beaver) |
| EM-1 (Erine1) | 126 | Mammalia | hedgehogs (Erinaceidae) | $1 \times 10^5$ |
| TAL (SINE_UT) | 237 | Mammalia | moles (Talpidae) | $1 \times 10^5$ |
| vic-1 (ALPINE1, ALPINE2, SINE_VV) | 117 | Mammalia | Camelidae | $10^5$ |
| Talua | 252 | Insecta | termites (Isoptera) | $1 \times 10^5$ |
| DIP (B2L_S) | 190 | Mammalia | Dipodidae & Zapodidae | $1 \times 10^5$ |
| VES (Ves2, Ves3, Ves4) | 191 | Mammalia | bat families Vespertilionidae, Molossidae, Phyllostomidae & Emballonuridae | $10^5$ |
| SOR | 157 | Mammalia | shrews (Soricidae) | $1 \times 10^5$ |
| MEN | 259 | Mammalia | squirrels *Menetes* & *Callosciurus* | $1 \times 10^5$ |
| ERI-2 (Erine2) | 186 | Mammalia | hedgehogs (Erinaceidae) | $1 \times 10^5$ |
| WallSI4 | 233 | Mammalia | wallaby (*Macropus eugenii*) | $1 \times 10^5$ |

TABLE 2-continued

SINE Table—FIG. 6

| SINE Σ: 213 (100%) | Length (w/o tail) | Taxon | Distribution | Copy number |
|---|---|---|---|---|
| LF (LFSINE_Vert) | 453 | Vertebrata | coelacanths & tetrapods (Sarcopterygii) | $10^5$ (*Latimeria menadoensis*) $3 \times 10^2$ (mammals) |
| IDL-Geo (DIPODE1, DIPODE2) | 190 | Mammalia | Geomyidae & Heteromyidae | $1 \times 10^5$ |
| Sepioth2B | 229 | Cephalopoda | Sepioteuthinae & Loliginidae | $9.4 \times 10^4$ |
| ERE-A (ERE-1x, ERE-4x) | 251 | Mammalia | horses (*Equus* spp.) | $9 \times 10^4$ |
| Sepioth2A | 293 | Cephalopoda | Sepioteuthinae | $9 \times 10^4$ |
| OK | 405 | Cephalopoda | Octopodidae | $8.5 \times 10^4$ |
| Ther-2 (MIR3) | 220 | Mammalia | marsupials & placentals | $8 \times 10^4$ (human) |
| Taluc | 387 | Insecta | termites (Isoptera) | $7.9 \times 10^4$ |
| DAS-IIb | 355 | Mammalia | nine-banded armadillo (*Dasypus novemcinctus*) | $6.5 \times 10^4$ (with DAS-IIa) |
| DAS-IIa | 208 | Mammalia | nine-banded armadillo (*Dasypus novemcinctus*) | $6.5 \times 10^4$ (with DAS-IIb) |
| CM-1 (SINEX-1_CM, SINE2-1_CM) | 308 | Chondrichthyes | ghost shark (*Callorhinchus milii*) | $6.5 \times 10^4$ |
| Talud | 261 | Insecta | termites (Isoptera) | $6.3 \times 10^4$ |
| SP-D-Geo (DIPODE3) | 225 | Mammalia | Geomyidae & Heteromyidae | $6.1 \times 10^4$ |
| Ruka | 230 | Arachnida | ixodid ticks | $6 \times 10^4$ (*Rhipicephalus appendiculatus*) |
| Feilai | 275 | Insecta | yellow fever mosquito (*Aedes aegypti*) | $6 \times 10^4$ |
| Ped-1 | 231 | Mammalia | springhare (*Pedetes capensis*) | $6 \times 10^4$ |
| Mar3 (WSINE1) | 128 | Mammalia | marsupials (Metatheria) | $5.3 \times 10^4$ (wallaby) |
| TS | 158 | Angiospermae | Solanaceae & Convolvulacea | $5 \times 10^4$ (tobacco) |
| Mac1 (WALLSI2) | 311 | Mammalia | kangaroos (Macropodoidea) | $4.5 \times 10^4$ (wallaby) |
| Cisc-1 | 290 | Tunicata | sea squirt (*Ciona* spp.) | $4 \times 10^4$ |
| Fc-1 (tSINE_Fc) | 105 | Mammalia | Carnivora | $4 \times 10^4$ - $6 \times 10^4$ (cat, dog, panda) |
| ACar-1 (SINE2-1_ACar) | 269 | Reptilia | green anole (*Anolis carolinensis*) | $3.9 \times 10^4$ |
| OR1 | 390 | Cephalopoda | *Octopus* spp. | $3.3 \times 10^4$ |
| SlmI | 227 | Actinopterygii | Salmonoidei | $3 \times 10^4$ |
| RSINE1 | 139 | Mammalia | mouse & rat | $3 \times 10^4$ (mouse) $1.6 \times 10^4$ (rat) |
| DAS-I | 76 | Mammalia | nine-banded armadillo (*Dasypus novemcinctus*) | $2.9 \times 10^4$ |
| OR2 | 270 | Cephalopoda | *Octopus* spp. | $2.8 \times 10^4$ |
| ID (BC1, CAVID, MUSID, RDRE1_RN, RNALUIII, STRID1) | 75 | Mammalia | rodents | $2.5 \times 10^4$ - $5 \times 10^5$ |
| Talub | 277 | Insecta | termites (Isoptera) | $2 \times 10^4$ |
| Bovc-Ta2 | 315 | Mammalia | Bovidae (cattle, goats & sheep) | $2 \times 10^4$ |
| Anolis SINE2 | 456 | Reptilia | Green anole (*Anolis carolinensis*) | $1.4 \times 10^4$ |
| MEG-RL (Meg_PVa) | 197 | Mammalia | megabats (Megachiroptera) | $1 \times 10^4$ |
| Au | 180 | Angiospermae | Poaceae, Fabaceae, | $1 \times 10^4$ |

TABLE 2-continued

SINE Table—FIG. 6

| SINE Σ: 213 (100%) | Length (w/o tail) | Taxon | Distribution | Copy number |
|---|---|---|---|---|
| (SINE2-1_ZM) | | | Solanaceae & Gramineae | (Aegilops) $1 \times 10^2$ (other plants) $10^4$-$10^5$ |
| CHRS (CHR-1, CHR-2, CHRS-S, SINE2-1_BT, CHRL, CHRL_BT, SINE2-1_BT, SINE2-2_BT, SINE2-3_BT) | 321 (120-340) | Mammalia | cetaceans, hippopotamuses ruminants & suiforms | |
| SlmII | 465 | Actinopterygii | Salmonoidei | $1 \times 10^4$ |
| SINE3 (AmnSINE1) | 561 | Amniota | Amniota | $1 \times 10^4$ (zebrafish) |
| Oegop | 371 | Cephalopoda | Oegopsida | $1 \times 10^4$ |
| Mad-1 (SINE-1_Mad) | 159 | Angiospermae | apple (*Malus × domestica*) | $9.5 \times 10^3$ |
| Pca-1 (SINE2-1_Pca) | 330 | Mammalia | hyrax (*Procavia capensis*) | $9.3 \times 10^3$ |
| B1 (pB1, pB1dx, STR1) | 135 | Mammalia | rodents | $8 \times 10^3$- $6.5 \times 10^5$ |
| EC-1 (SINE2-1_EC) | 398 | Mammalia | horse (*Equus caballus*) | $7.7 \times 10^3$ |
| Gecko | 188 | Insecta | yellow fever mosquito (*Aedes aegypti*) | $7.2 \times 10^3$ |
| MEG-RS | 120 | Mammalia | megabats (Megachiroptera) | $7 \times 10^3$ |
| FabaS-VII | 124 | Angiospermae | barrel medic (*Medicago truncatula*) | $6.9 \times 10^3$ |
| p-SINE1 (p-SINE2, p-SINE3, SINE1R5_OS, SINE1OS, SINE6_OS, SINE8_OS, SINE16_OS) | 115 | Angiospermae | rice (*Oryza* genus) | $6 \times 10^3$ (rice) |
| STRIDM | 199 | Mammalia | thirteen-lined ground squirrel (Spermophilus tridecemlineatus) | $5.4 \times 10^3$ |
| BmSE | 249 | Insecta | silkworm (*Bombyx mori*) | $5.2 \times 10^3$ |
| Asu1 | 407 | Insecta | mosquito (*Armigeres subalbatus*) | $5.1 \times 10^3$ |
| MEG-TR | 182 | Mammalia | megabats (Megachiroptera) | $5 \times 10^3$ |
| DR-2 (SINE2-1_DR, CypS-I) | 174 | Actinopterygii | zebrafish (*Danio*) | $5 \times 10^3$ |
| DR-1 (SINE_DR1) | 244 | Actinopterygii | zebrafish (*Danio*) | $4.8 \times 10^3$ |
| PTr-1 (SINE2-1_PTr, SaliS-I) | 187 | Angiospermae | black cottonwood (*Populus trichocarpa*) | $4.1 \times 10^3$ |
| PTr-2 (SINE2-2_PTr, SaliS-II) | 161 | Angiospermae | black cottonwood (*Populus trichocarpa*) | $4 \times 10^3$ |
| SP-7 (SINE2-7_SP) | 199 | Echinoidea | *Strongylocentrotus purpuratus* | $4 \times 10^3$ |
| MEG-T2 | 212 | Mammalia | megabats (Megachiroptera) | $4 \times 10^3$ |
| Lj-1 (Lj_SINE-1) | 135 | Angiospermae | *Lotus japonicus* & *Medicago truncatula* | $3.1 \times 10^3$ (*Lotus japonicus*) $3.9 \times 10^1$ (*Medicago truncatula*) |
| CQ-6 (SINE6_CQ) | 208 | Insecta | mosquito (*Culex pipiens*) | $3.1 \times 10^3$ |

TABLE 2-continued

SINE Table—FIG. 6

| SINE | Length (w/o tail) | Taxon | Distribution | Copy number |
| --- | --- | --- | --- | --- |
| Σ: 213 (100%) | | | | |
| FabaS-IX | 120 | Angiospermae | certain Fabales | $3 \times 10^3$ (*Glycine max*) $2.8 \times 10^2$ (*Cajanus cajan* & *Medicago truncatula*) |
| FabaS-I (MT_SINE-1) | 131 | Angiospermae | barrel medic (*Medicago truncatula*) | $2.8 \times 10^3$ |
| EuphS-I | 83 | Angiospermae | certain Euphorbiaceae | $2.5 \times 10^3$ (*Manihot esculenta*) $1.3 \times 10^2$ (*Ricinus communis*) |
| CQ-3 (SINE3_CQ) | 404 | Insecta | mosquito (*Culex pipiens*) | $2.5 \times 10^3$ |
| Lam1 | 230 | Hyperoartia | lamprey (*Lethenteron reissneri*) | $2.4 \times 10^3$ |
| AFC-2 (SINE2-1_AFC) | 275 | Actinopterygii | African cichlids | $2.4 \times 10^3$ |
| FabaS-II (SINE1_MT, MT-1) | 116 | Angiospermae | barrel medic (*Medicago truncatula*) | $2.2 \times 10^3$ |
| SP-4 (SURF1, SINE2-4_SP) | 262 | Echinoidea | *Strongylocentrotus purpuratus* | $2.1 \times 10^3$ |
| Sine200 (SINEX-1/2) | 190 | Insecta | mosquito *Anopheles gambiae* | $2 \times 10^3$ |
| SolS-I | 179 | Angiospermae | Solanaceae | $2 \times 10^3$ (potato) $1.4 \times 10^3$ (*N. benthamiana*) $6.3 \times 10^2$ (tomato) |
| AFC (SINE_AFC) | 310 | Actinopterygii | African cichlids | $2 \times 10^3$- $2 \times 10^4$ |
| SolS-II (SINE2-1_STu) | 216 | Angiospermae | Solanaceae | $1.7 \times 10^3$ (potato, tomato) $2.2 \times 10^3$ (*N. benthamiana*) |
| FabaS-VIII | 115 | Angiospermae | barrel medic (*Medicago truncatula*) | $1.6 \times 10^3$ |
| HaSE2 (HaSE2_DP) | 284 | Insecta | certain owlet moths (*Helicoverpa, Heliothis* & *Spodoptera*) & monarch butterfly (*Danaus plexippus*) | $1.6 \times 10^3$ (*Danaus plexippus*) |
| FabaS-VI | 185 | Angiospermae | certain Fabales | $1.4 \times 10^3$ (*Cajanus cajan*) $4.6 \times 10^2$ (*Medicago truncatula*) |
| CQ-2 (SINE2-2_CQ) | 238 | Insecta | mosquito (*Culex pipiens*) | $1.4 \times 10^3$ |
| VitaS-I | 93 | Angiospermae | grapevine (*Vitis vinifera*) | $1.3 \times 10^3$ |
| SolS-IIIa | 231 | Angiospermae | Solanaceae | $1.3 \times 10^3$ (potato) $1 \times 10^3$ (tomato) |
| SP-5 (SPEC1, SINE2-5_SP) | 225 | Echinoidea | *Strongylocentrotus purpuratus* | $1.3 \times 10^3$ |
| SolS-V | 107 | Angiospermae | Solanaceae | $1.2 \times 10^3$ (potato) $5.4 \times 10^2$ (tomato) $4.3 \times 10^2$ (*N. benthamiana*) |
| OsSN2 (SINE9_OS, SINE2-11_SBi, SINE2-12_SBi) | 283 | Angiospermae | rice & sorghum (*Oryza sativa* & *Sorghum bicolor*) | $1.2 \times 10^3$ (rice) $2.2 \times 10^2$ (sorghum) |
| Mad-2 (SINE-2_Mad, SINE-4_Mad) | 193 | Angiospermae | apple (*Malus × domestica*) | $1 \times 10^3$ |

TABLE 2-continued

SINE Table—FIG. 6

| SINE<br>Σ: 213 (100%) | Length<br>(w/o tail) | Taxon | Distribution | Copy number |
|---|---|---|---|---|
| ScroS-I | 210 | Angiospermae | Common monkey-flower<br>(*Mimulus guttatus*) | $1 \times 10^3$ |
| Smα<br>(Sjα, T2) | 332 | Trematoda | Schistosomatidae | $1 \times 10^3$ |
| HE1 | 340 | Chondrichthyes | higher elasmobranches | $10^3$-$10^6$ |
| SolS-IV | 193 | Angiospermae | Solanaceae | $1 \times 10^3$<br>(potato)<br>$4.7 \times 10^2$<br>(*N. benthamiana*)<br>$3.7 \times 10^2$<br>(tomato) |
| SP-1<br>(SINE2-1_SP) | 246 | Echinoidea | *Strongylocentrotus<br>purpuratus* | $9.9 \times 10^2$ |
| SolS-VI | 225 | Angiospermae | Solanaceae | $9.5 \times 10^2$<br>(*N. benthamiana*)<br>$1 \times 10^2$<br>(potato) |
| TguSINE1 | 124 | Aves | Estrildidae | $9.4 \times 10^2$ |
| CucuS-II | 98 | Angiospermae | Cucurbitaceae | $8.7 \times 10^2$<br>(*Cucumis sativus*) |
| CQ-5<br>(SINE5_CQ) | 237 | Insecta | mosquito<br>(*Culex pipiens*) | $8.4 \times 10^2$ |
| AFC-3<br>(SINE3_AFC) | 215 | Actinopterygii | African cichlids | $8 \times 10^2$ |
| OsSN3<br>(CASINE) | 176 | Angiospermae | rice<br>(*Oryza sativa*) | $7.1 \times 10^2$ |
| CucuS-I | 206 | Angiospermae | Cucurbitaceae | $7.1 \times 10^2$<br>(*Cucumis sativus*) |
| SaliS-V | 268 | Angiospermae | black cottonwood<br>(*Populus trichocarpa*) | $7 \times 10^2$ |
| FabaS-IV | 205 | Angiospermae | barrel medic<br>(*Medicago truncatula*) | $6.9 \times 10^2$ |
| FabaS-III<br>(MT_SINE-3) | 166 | Angiospermae | barrel medic<br>(*Medicago truncatula*) | $6.9 \times 10^2$ |
| Xt-2<br>(SINE2-1_XT) | 318 | Amphibia | *Xenopus tropicalis* | $6 \times 10^2$ |
| OsSN1<br>(F524) | 285 | Angiospermae | rice<br>(*Oryza sativa*) | $5.7 \times 10^2$ |
| Squam-2 | 191 | Reptilia | scaled reptiles<br>(Squamata) | $5.6 \times 10^2$<br>(anole) |
| CQ-1<br>(SINE2-1_CQ) | 662 | Insecta | mosquito<br>(*Culex pipiens*) | $5.5 \times 10^2$ |
| Lj-3<br>(Lj_SINE-3) | 182 | Angiospermae | *Lotus japonicus* | $5.5 \times 10^2$ |
| Twin | 217 | Insecta | mosquito<br>(*Culex* spp.) | $5 \times 10^2$ |
| MamSINE1 | 286 | Mammalia | mammals<br>(platypus) | $5 \times 10^2$ |
| SaliS-III | 168 | Angiospermae | black cottonwood<br>(*Populus trichocarpa*) | $4.9 \times 10^2$ |
| BraS-I | 134 | Angiospermae | Brassicaceae | $4.6 \times 10^2$<br>(*Arabidopsis lyrata*)<br>$3.2 \times 10^1$<br>(*Arabidopsis thaliana*) |
| SB10<br>(Bos d, e) | 159 | Angiospermae | *Brassica oleracea* | 455 |
| SP-6<br>(SINE2-6_SP) | 342 | Echinoidea | *Strongylocentrotus<br>purpuratus* | $4.5 \times 10^2$ |
| SB9<br>(Bos c, f) | 212 | Angiospermae | *Brassica oleracea* | 395 |
| GA-1<br>(SINE2-1_GA) | 294 | Actinopterygii | stickleback<br>(*Gasterosteus aculeatus*) | $3.4 \times 10^2$ |
| Lj-2<br>(Lj_SINE-2) | 191 | Angiospermae | *Lotus japonicus* | $3.3 \times 10^2$ |
| SB1<br>(S1) | 171 | Angiospermae | *Brassica oleracea* | 330 |
| SaliS-IV | 185 | Angiospermae | black cottonwood<br>(*Populus trichocarpa*) | $3.2 \times 10^2$ |
| SolS-VII | 211 | Angiospermae | Solanaceae | $3 \times 10^2$<br>(*N. benthamiana*)<br>$3.4 \times 10^1$<br>(tomato) |
| FR-1<br>(SINE_FR1) | 273 | Actinopterygii | fugu<br>(*Takifugu rubripes*) | $3 \times 10^2$ |
| SP-2 | 231 | Echinoidea | *Strongylocentrotus* | $2.9 \times 10^2$ |

TABLE 2-continued

SINE Table—FIG. 6

| SINE<br>Σ: 213 (100%) | Length<br>(w/o tail) | Taxon | Distribution | Copy number |
|---|---|---|---|---|
| (SINE2-2_SP) | | | *purpuratus* | |
| SB14<br>(Bos j, k) | 156 | Angiospermae | *Brassica oleracea* | 285 |
| PinS-I | 227 | Pinophyta | spruces<br>(*Picea* spp.) | $2.7 \times 10^2$ |
| PTr-3 | 183 | Angiospermae | black cottonwood<br>(*Populus trichocarpa*) | $2.6 \times 10^2$ |
| FabaS-V | 185 | Angiospermae | certain Fabales | $2.4 \times 10^2$<br>(*Medicago truncatula*)<br>$\sim 4 \times 10^1$<br>(*Glycine max* & *Lotus japonicus*) |
| SB8 | 95 | Angiospermae | *Brassica oleracea* | 215 |
| Ras1 | 281 | Actinopterygii | *Rasbora pauciperforata* | $2 \times 10^2$ |
| CELE45 | 250 | Nematoda | Caenorhabditis elegans | $2 \times 10^2$ |
| AC1<br>(SINE_FR2,<br>SINE_TE) | 380 | Actinopterygii | fugu & medaka | $2 \times 10^2$<br>(fugu)<br>$3 \times 10^3$<br>(medaka) |
| SolS-IIIb | 246 | Angiospermae | Solanaceae | $1.6 \times 10^2$<br>(potato, *N. benthamiana*)<br>$1 \times 10^2$<br>(tomato) |
| 5S-Sauria | 236 | Reptilia | green anole<br>(*Anolis carolinensis*) | $1.6 \times 10^2$ |
| SB12<br>(Bos i1) | 170 | Angiospermae | *Brassica oleracea* | 150 |
| SB2<br>(RAthE1, SN2) | 149 | Angiospermae | *Arabidopsis thaliana* &<br>*Brassica oleracea* | 144<br>(*Arabidopsis*)<br>165<br>(*Brassica*) |
| PoaS-II | 156 | Angiospermae | purple false brome<br>(*Brachypodium distachyon*) | $1.4 \times 10^2$ |
| PoaS-I | 156 | Angiospermae | purple false brome<br>(*Brachypodium distachyon*) | $1.4 \times 10^2$ |
| CQ-4<br>(SINE4_CQ) | 583 | Insecta | mosquito<br>(*Culex pipiens*) | $1.4 \times 10^2$ |
| SP-3<br>(SINE2-3_SP) | 353 | Echinoidea | *Strongylocentrotus purpuratus* | $1.4 \times 10^2$ |
| Sma I<br>(Fok I, pol<br>III/SINE,<br>SMAIDIV,<br>SINE_SM) | 150 | Actinopterygii | Salmonoidei | $1 \times 10^2$-<br>$3 \times 10^4$ |
| Cre-1<br>(SINEX-1_CR) | 520 | Chlorophyta | *Chlamydomonas reinhardtii* | $1 \times 10^2$ |
| Hpa I<br>(OM2) | 200 | Actinopterygii | Salmonoidei | $10^2$-$10^4$ |
| SBi-1<br>(SINE2-1_SBi) | 282 | Angiospermae | *Sorghum bicolor* | $1 \times 10^2$ |
| MARE3 | 172 | Mammalia | mammals | $1 \times 10^2$<br>(human)<br>$1.4 \times 10^3$<br>(opossum) |
| Tu type II<br>(TUBE4) | 278 | Mammalia | tree shrews<br>(Scandentia) | 102 |
| SB11<br>(Bos G) | 170 | Angiospermae | *Brassica oleracea* | 100 |
| Ava III | 260 | Actinopterygii | Salmonoidei | $1 \times 10^2$ |
| UCON3 | 168 | Euteleostomi | Euteleostomi | 102 |
| Tu type I<br>(TUBE2,<br>TUBE3,<br>TUBE5) | 179 | Mammalia | tree shrews<br>(Scandentia) | 102 |
| NV-1<br>(SINE2-1_NV) | 257 | Anthozoa | starlet sea anemone<br>(*Nematostella vectensis*) | 95 |
| NV-2<br>(SINE2-2_NV) | 324 | Anthozoa | starlet sea anemone<br>(*Nematostella vectensis*) | 70 |
| SB4<br>(RAthE3, SN1) | 159 | Angiospermae | *Arabidopsis thaliana* | 64 |
| NV-3<br>(SINE2-3_NV) | 376 | Anthozoa | starlet sea anemone<br>(*Nematostella vectensis*) | 60 |

TABLE 2-continued

SINE Table—FIG. 6

| SINE<br>Σ: 213 (100%) | Length<br>(w/o tail) | Taxon | Distribution | Copy number |
|---|---|---|---|---|
| SB3<br>(RAthE2, RBolE2) | 297 | Angiospermae | Arabidopsis thaliana & Brassica oleracea | 58<br>(Arabidopsis)<br>510<br>(Brassica) |
| SB13<br>(Bos i2) | 225 | Angiospermae | Brassica oleracea | 55 |
| SB15<br>(Bos 1) | 206 | Angiospermae | Brassica oleracea | 40 |
| SB6<br>(ATSINE4) | 297 | Angiospermae | Arabidopsis thaliana & Brassica oleracea | 32<br>(Arabidopsis) 735<br>(Brassica) |
| Cre-4<br>(SINEX-4_CR) | 500 | Chlorophyta | Chlamydomonas reinhardtii | 30 |
| Cre-3<br>(SINEX-3_CR) | 496 | Chlorophyta | Chlamydomonas reinhardtii | 30 |
| SB5<br>(Bos a, ab, b, ai) | 162 | Angiospermae | Arabidopsis thaliana & Brassica oleracea | 7<br>(Arabidopsis) 645<br>(Brassica) |
| Asu2 | 313 | Insecta | mosquito (Armigeres subalbatus) | $6 \times 10^3$ |
| SB7 | 352 | Angiospermae | Arabidopsis thaliana & Brassica oleracea | 3<br>(Arabidopsis) 210<br>(Brassica) |
| EbuSINE1 | 345 | Myxini | hagfish<br>(Eptatretus burgeri) | |
| BflSINE1 | 363 | Leptocardii | lancelet | |
| SacSINE1 | 454 | Chondrichthyes | dogfish shark<br>(Squalus acanthias) | |
| Rhin-1 | 190 | Mammalia | bat families Rhinolophidae & Hipposideridae | |
| OS | 469 | Actinopterygii | Salmonoidei | |
| SK | 241 | Cephalopoda | squid<br>(Loligo bleekeri) | |
| LmeSINE1 | 314 | Sarcopterygii | coelacanth<br>(Latimeria menadoensis) | |
| Idio2 | 425 | Cephalopoda | Japanese pygmy squid<br>(Idiosepius paradoxus) | |
| Idio1 | 259 | Cephalopoda | Japanese pygmy squid<br>(Idiosepius paradoxus) | |
| EbuSINE2 | 345 | Myxini | hagfish<br>(Eptatretus burgeri) | |
| MyrSINE | 83 | Mammalia | anteaters<br>(Myrmecophagidae) | |
| HaSE1<br>(HzIS1) | 375 | Insecta | certain owlet moths<br>(Helicoverpa & Heliothis) | |
| Otri | 252 | Insecta | mosquito<br>Ochlerotatus triseriatus | |
| NymS-I | 131 | Angiospermae | spatterdock<br>(Nuphar advena) | |
| HaSE3 | 354 | Insecta | certain owlet moths<br>(Helicoverpa, Heliothis, Trichoplusia & Mamestra) | | belongs and by reference to published texts, which provide one skilled in the art with a general guide to many of the terms used in the present application. The definitions contained in this specification are provided for clarity in describing the components and compositions herein and are not intended to limit the claimed invention.

It is to be noted that the term "a" or "an" refers to one or more. As such, the terms "a" (or "an"), "one or more," and "at least one" are used interchangeably herein. The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

As used herein, genomic DNA refers to chromosomal DNA of the subject organism. Subject "organisms" or "subjects" or "patients" include, without limitation, an organism, such as an animal, such as Homo sapiens (human), Mus musculus (mouse), Rattus norvegicus (rat), Oryctolagus cuniculus (rabbit), Canis lupus familiaris (dog), Danio rerio (zebrafish), Drosophila melanogaster (fruit fly), Caenorhabditis elegans (roundworm), Sus scrofa (pig), Bos taurus (cow), Ovis aries (sheep), Capra aegagrus hircus (goat), non-human primates and insects; plant, such as crops and algae; fungi, bacterial, archaea, yeast, virus, protozoans, amebas and the like. Subject organisms can be selected by the person of skill in the art. It is also intended that genomic DNA can refer to a portion, rather than the totality, of the chromosomal DNA of an organism. Such portion may be contained within a plasmid, e.g. a bacterial artificial chromosome (BAC), or may be isolated.

The following examples illustrate several aspects and embodiments of the invention. As shown in the examples, the flexible and efficient fluorescent tagging of specific sequences allow us to obtain context specific sequence information along the long linear DNA molecules in the BioNano Genomics nanochannel. Our global nick-labeling scheme tags short recognition sequences, whose spatial relation can be translated into a genomic map. Not only can this integrated fluorescent DNA double strand labeling make the whole genome mapping more accurate, and provide more information, but it can also specifically target certain loci for clinical testing. Importantly, it renders the labeled double-stranded DNA available in long intact stretches for high-throughput analysis in nanochannel arrays as well as for lower throughput targeted analysis of labeled DNA regions using alternative methods for stretching and imaging the labeled large DNA molecules. Thus, this method will dramatically improve both automated high-throughput genome-wide mapping as well as targeted analyses of complex regions containing repetitive and structurally variant DNA.

Figure 2:
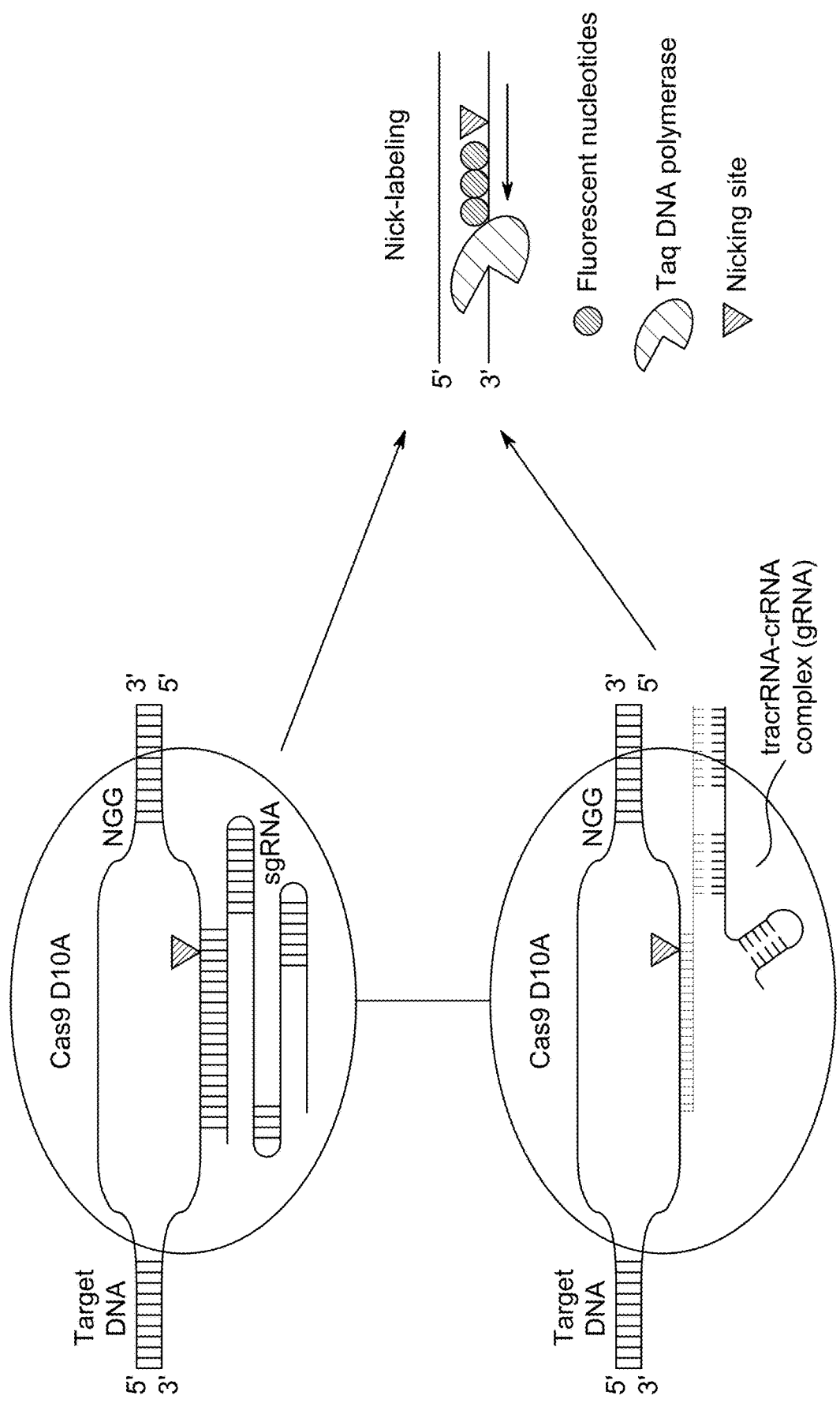
FIG. 2 is a schematic graph illustrating Cas9n/gRNA target sequence specific fluorescent labeling for whole genome DNA mapping. The Cas9n fluorescent nick-labeling system uses a guide RNA (gRNA) to direct the Cas9 nuclease to a targeted site. The gRNA is composed of a trans-activating crRNA (tracrRNA) and a crRNA that contains a 20 nucleotide sequence that is complementary to the site of interest. A mutation in the RuvC-like domain nuclease alters the Cas9 enzyme to make only a single cut three nucleotides upstream of a protospacer adjacent motif (PAM) of the 3'-5' strand of the target DNA. In the nick labeling method, after Cas9n D10A generates a nick, fluorophores are directly incorporated to the nick sites using Taq DNA Polymerase. These fluorophores can be detected using fluorescence microscopy.

We incorporated the CRISPR-Cas9 technology into our nick-labeling procedure for targeted, sequence-specific nicking and fluorescent labeling in one color, followed by global nickase enzyme motif-dependent labeling in a second color. We used two different forms of guide RNAs. For the HIV-plasmid experiments, the target sequence was cloned, amplified and then in vitro transcribed to result in an expressed single guide RNA (sgRNA). For all other experiments, the CRISPR RNAs (crRNAs) and transactivating CRISPRRNA (tracrRNA) were purchased from GE Dharmacon and pre-incubated to form each guide RNA (gRNA). In both cases, the gRNA-directed Cas9n D10A makes a precise single cut in one strand of the target double-strand DNA three nucleotides upstream of a protospacer adjacent motif (PAM) and fluorescent nucleotides are directly incorporated to these specific nick sites using Taq DNA Polymerase (FIG. 2). This approach promises to dramatically improve DNA mapping in complex and structurally variant genomic regions, as well as facilitate high-throughput automated whole-genome mapping.

Figure 3A:
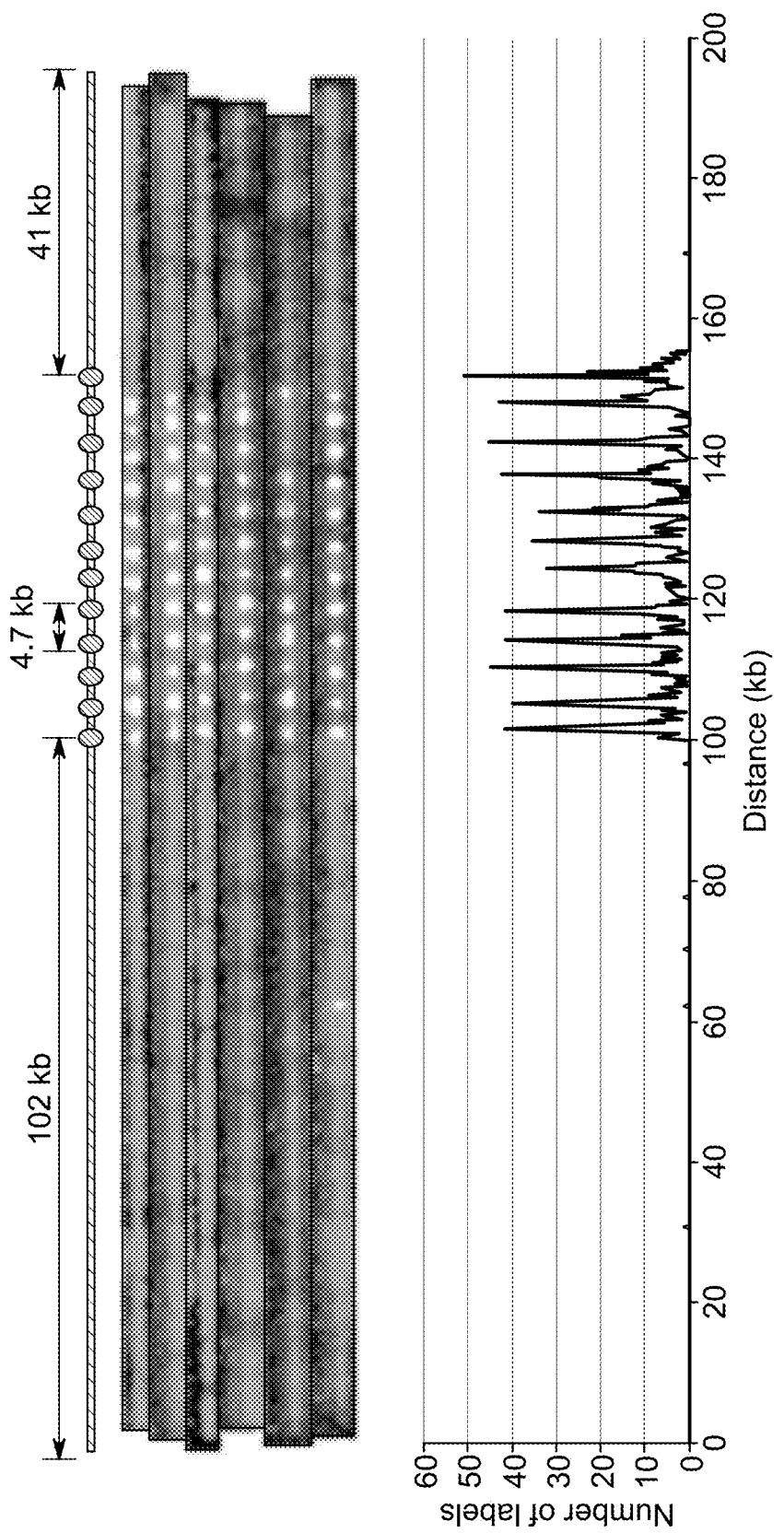
FIG. 3A is a graph showing an example result of Cas9n-nick labeling. The expected labeling pattern and distances between labels is shown above corresponding fluorescent microscopy images. A single copy of HLS DUF1220 triplet is approximately 4.7 kb, which cannot be identified with the sequence-motif labeling method due to lack of recognition sites within the repeat region. The Cas9n fluorescent nick-labeling method was able to label this region using a gRNA designed to the DUF1220 triplet. These recognition sites were labeled with fluorescent labels. The tandem repeats were separated approximately 4.7 kb as predicted. The histogram of the DUF1220 gRNA labels is shown below the molecules. A total of 192 molecules were evaluated for the labeling efficiency.

We first established the Cas9n fluorescent nick-labeling conditions and investigated the labeling efficiency with BAC clones, fosmids and plasmids as model systems. FIG. 3A shows the Cas9n fluorescent nick-labeling results of HLS DUF1220 triplets on a BAC clone. The histogram of the label distribution is shown in the bottom graph of FIG. 3A. Genome sequences encoding DUF1220 protein domains have undergone an exceptional human lineage specific (HLS) increase in copy number, which is implicated in human brain size, pathology and evolution (22). A single copy of HLS DUF1220 triplet spans about 4.7 kb, and there are 12 copies on the BAC clone CH17-353B19. A gRNA probe was designed to target one unit of the triplets. Clearly, there are 12 copies detected on this 240 kb BAC clone and the distance between the each tripletmeasures 4.7 kb, which is in a good agreement with the clone sequence. The labeling efficiency of each locus was determined by evaluating 192 labeled BAC molecules, ranging from 87% to 98%. Interestingly, the middle copies (#6-8 labels from the left most label in FIG. 3A) are labeled at lower labeling efficiency. The Cas9n fluorescent nick-labeling is very specific.

Figure 3B:
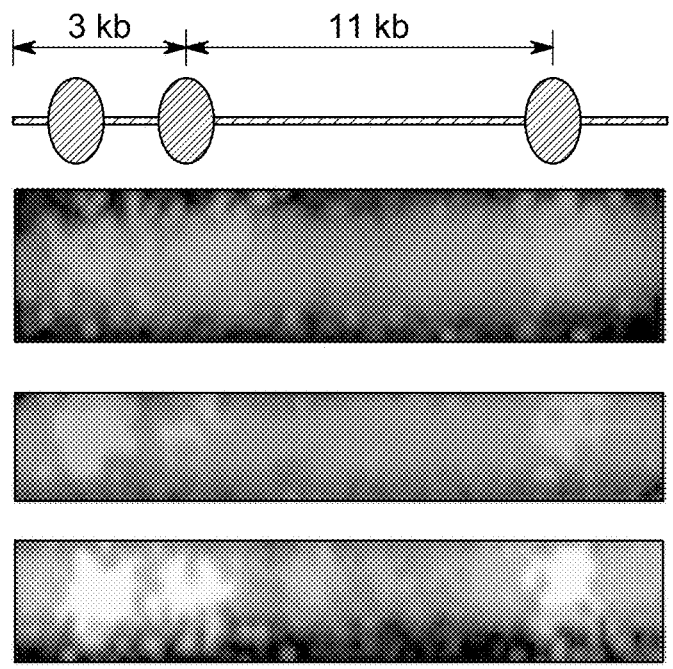
FIG. 3B shows fluorescent microscopy images of three sgRNAs targeting three different locations (Gag, Pol, Env) within the HIV-1 genome. The sites were correctly labeled with the expected distances between each sgRNA. The image shows the linearized DNA after EcoRI digestion.
Figure 3C:
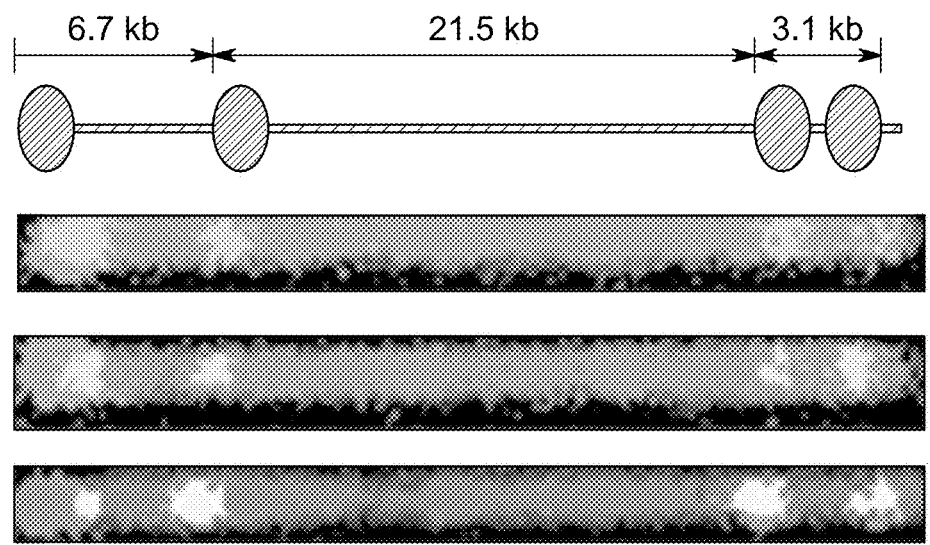
FIG. 3C shows fluorescent microscopy images of three gRNAs targeting the chromosome 1q subtelomere which generated the expected pattern.

The extra labels outside of the DUF domain were used to calculate the false positives in FIG. 3A. The spurious labels inside the DUF domain are harder to define because the DNA molecules inside the nanochannel are not static. Their slight movements and the limitation of optical resolution may cause inaccurate measurement of 4.7 kb repetitive sequences during the imaging time (200 ms). When all of the spurious spots inside and outside of the DUF domain were used, the false positive percentage is 0.6%. Next, we applied the Cas9n fluorescent nick-labeling method to a plasmid containing the HIV-1 genome. HIV-1 integrates into the human genome at different locations (23), each of which may be identifiable directly through an appropriate integration site labeling and global genome mapping strategy. Identification of such sites in HIV-1 latent cells is essential for understanding the molecular and epigenetic mechanisms underlying HIV-1 latency (24). Similarly, this sequence-specific mapping approach could be used to identify lentivirus random integration sites in the host cells, which may disrupt both endogenous gene expression and vector gene expression patterns (25). Multiple sgRNAs were designed and tested to target HIV-1 structural region (Gag, Pol, Env) to determine the most effective gRNA that labels the HIV-1 genome. The sites were correctly labeled with the expected distances between each sgRNA (FIG. 3B). However, the labeling efficiencies at each site of 36%, 58% and 44% from the left most label respectively, suggesting that labeling efficiency may be sequence- or region-dependent. It could also be the difference in labeling efficiency of sgRNA versus gRNA. The labeling efficiencies of the gRNAs were much higher than those achieved using sgRNAs. In a third model system, a fosmid containing a subtelomeric segment of human 1q ending in 100 bases of (TTAGGG)n was used to test the Cas9n fluorescent nick-labeling. We designed four guide RNA probes to target the (TTAGGG)n tract and three distinct loci on the subtelomere. The labeling pattern matches very closely with the positions of the gRNA seed sequences in the 1q reference sequence (FIG. 3C). However, the labeling efficiency is relatively lower for the telomere with 30%, while the labeling efficiency of subtelomeric markers are 95%, 79% and 99% respectively from the left most left label on 1q (FIG. 3C). This may be due to non-Watson-Crick pairings of the hexameric repeats, the high G+C content or the secondary structure of guide RNA probes targeting the (TTAGGG)n repeat.

We next tested the combination of Cas9n fluorescent nick-labeling with nicking endonuclease based sequence motif labeling. This approach has the potential to find wide applications in whole genome mapping of repetitive sequences as well as genotyping of structural variations and identification/mapping of viral integration sites. In FIG. 4A, the DUF1220 triplet repeats were first labeled with Cas9n fluorescent nick-labeling of red fluorescent nucleotides. These labeled DNA molecules were then globally nick-labeled with green nucleotides using Nt.BspQI to target the GCTCTTC motif. Twelve copies of DUF1220 triplets were detected spanning about 52 kb. Only the flanking regions of this 52 kb were shown to have the GCTCTTC motif, which can be mapped to reference genome to indicate the genomic locations of the DUF1220 triplet array. The histogram of the label distribution is shown in the bottom graph of FIG. 4A. Clearly, the combination of Cas9n fluorescent nick-labeling and nicking endonuclease sequence motif labeling, not only can detect the copy numbers of the DUF1220 triplets, but also can map the locations of the repeats.

The same approach was also applied to measure the telomere repeat length of a telomere-terminal fragment of chromosome 8q cloned in a fosmid. This fosmid carries 800 bp of the repetitive (TTAGGG)n sequence, which lacks motif nicking sites recognized by currently available nicking endonucleases and therefore cannot be labeled with current sequence-motif based methods. A gRNA specific for the telomere was designed. In FIG. 4B, the telomere was first labeled with Cas9n fluorescent nick-labeling of red fluorescent nucleotides. The labeled DNA molecules were then labeled with green nucleotides by Nt.BspQI nick-labeling to target the GCTCTTC motif. The telomere was correctly labeled on the end of the sequence. The length of this telomere region can be determined by measuring the length of the red fluorophore region and the intensity of its fluorescence relative to known controls after imaging. Sequence motif labeling over extended subtelomere regions linked on single large DNA molecules to the Cas9n fluorescent nick labeling (TTAGGG)n can be used to identify the specific subtelomere by comparison with genome-wide maps.

Figure 5A:
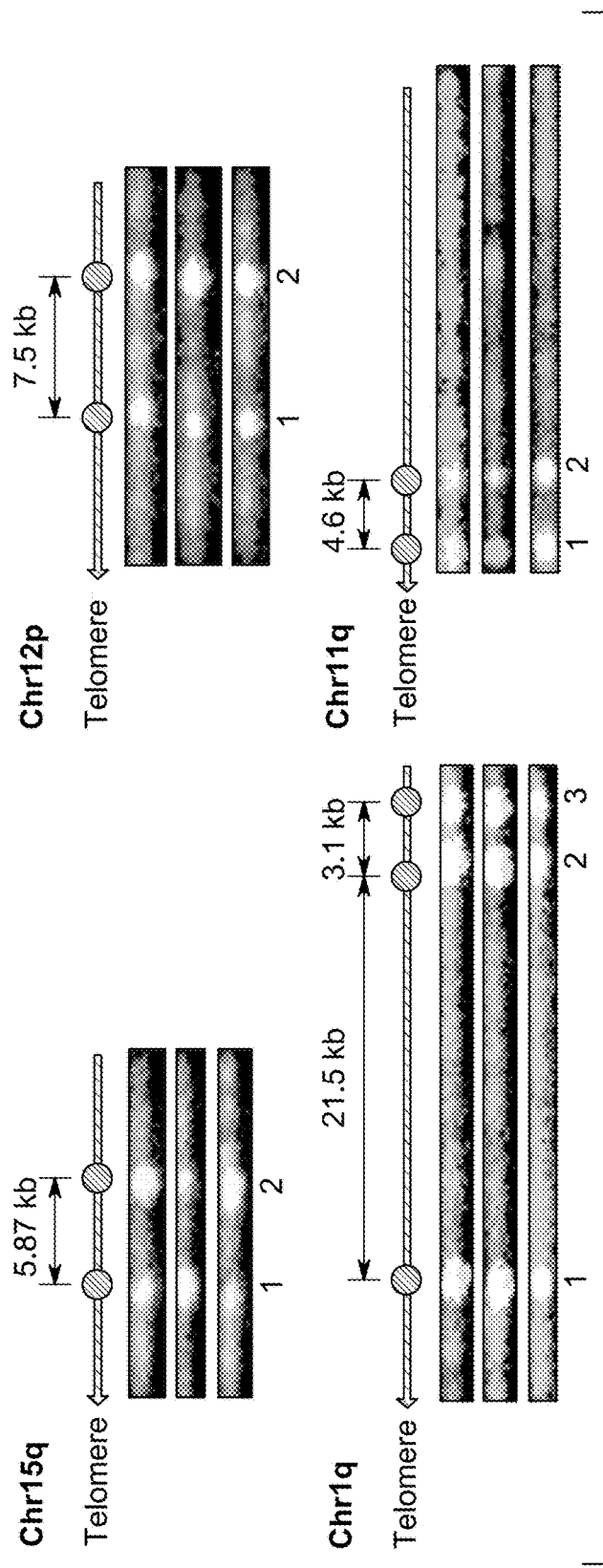
FIG. 5A shows graphs illustrating Cas9n fluorescent nick-labeling created locus-specific and variant-specific barcodes. The expected labeling pattern and distances between labels are shown above corresponding fluorescent microscopy images. For each of the tested subtelomere regions specific gRNAs were designed and pooled in the in vitro nicking reaction mix in order to produce a unique pattern. In each instance, the expected pattern of the red fluorophores in the Cas9n fluorescent nick-labeling system was obtained.
Figure 5B:
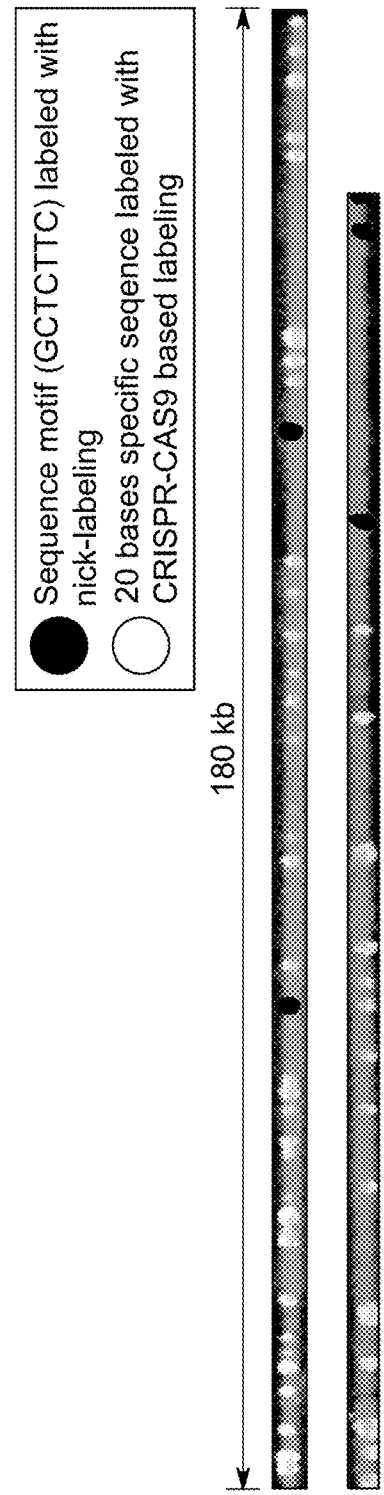
FIG. 5B is a graph of human genomic DNA was labeled with Alu gRNAs, and followed by conventional sequence-motif labeling with Nt.BspQI. Conventional sequence-motif dependent labeling sites (black circles/ovals) were found infrequently within these genomic DNA regions. However, Alu-specific gRNAs directed Cas9n D10A to generate information-rich long-range barcoding patterns (white circles/ovals).

Cas9n fluorescent nick-labeling can be used to create locus-specific and variant-specific barcodes. We designed gRNAs to create barcodes to distinguish individual subtelomeres linked on single molecules to (TTAGGG)n tracts (FIG. 5A, Chr 1q and Chr 11q) and to distinguish variant copies of highly similar subtelomeric segmental duplications (Chr 15q and Chr 12p) using the Cas9n sequence specific labeling methods. It has been suggested that the shortest telomere or a small subset of the shortest telomeres in a cell determines the onset of senescence, apoptosis or genome instability (26, 27), the ability to systematically measure individual dysfunctionally short (TTAGGG)n tracts (rather than average telomere tract lengths in a sample as is typically measured currently) would provide important new high-resolution information on specific telomere functional status and identity at the single-molecule level. On the telomeric fosmids from Chr 15q and Chr 12p (FIG. 5A), Cas9n-gRNA directed nicks at two loci in a segmentally duplicated subtelomere region containing the WASH gene family (Linnardopoulou et al., 2007) were labeled in red. The same pair of gRNAs generated signals separated by 5.87 kb on the 15q fosmid and 7.5 kb on Chr 12p fosmid, as predicted by the reference sequences of these two highly similar but structurally non-identical regions. The patterns generated by three target-specific gRNAs on Chr1q and two gRNAs on 11 q are unique, easily distinguishable from each other and from both of the WASH gene-related patterns, and correspond exactly to what is expected from their respective reference sequences. These initial experiments indicate that specific gRNAs can be pooled to generate multiple specific nicks that, when labeled, can create custom barcodes predicted precisely by the respective reference sequences. FIG. 5B shows the results of experiments combining the Cas9n fluorescent nick-labeling and nicking endonuclease sequence motif labeling to map Alu elements in the human genome. Alu sequences, with about one million copies, are the most abundant retroelements in humans, and account for up 10% of the human genome. These SINE (Short Interspersed Nuclear Elements) sequences, exclusively found in primate genomes, have been particularly active in the human lineage even after human-chimpanzee divergence, where they are theorized to have contributed to some of the human-specific characteristics such as brain size.

A gRNA sequence was designed to target 280 000 Alu sites out of one million copies. Typical genomic DNA molecules are imaged and shown in FIG. 5B. One 180 kb molecule displays dense Alu elements with only two GCTCTTC motifs. Another DNA molecule shows dense Alu elements with two GCTCTTC motifs. The combined information can be used to map the DNA molecules to the reference genome and profile the distribution of Alu elements on the whole genome scale.

We have demonstrated the capabilities of our integrated approach of sequence motif fluorescent tagging and sequence specific labeling with Cas9n fluorescent nick-labeling system. The flexible and efficient fluorescent tagging of specific sequences allow us to obtain context specific sequence information along the long linear DNA molecules in the BioNano Genomics nanochannel. Our global nick-labeling scheme tags short recognition sequences, whose spatial relation can be translated into a genomic map. Not only can this integrated fluorescent DNA double strand labeling make the whole genome mapping more accurate, and provide more information, but it can also specifically target certain loci for clinical testing. Importantly, it renders the labeled double-stranded DNA available in long intact stretches for high-throughput analysis in nanochannel arrays as well as for lower throughput targeted analysis of labeled DNA regions using alternative methods for stretching and imaging the labeled large DNA molecules. Thus, this method will dramatically improve both automated high-throughput genome-wide mapping as well as targeted analyses of complex regions containing repetitive and structurally variant DNA. The publication McCaffrey et al, Nucleic Acids Research, 2015, 44(2):e11 doi: 10.1093/nar/gkv878 is specifically incorporated herein by reference in its entirety.

EXAMPLE 1—Preparation of DNA Samples and Guide RNA

Target sequence-specific labeling with Cas9n fluorescent nick-labeling was carried out on the BAC clone CH17-353B19, fosmids carrying cloned telomere-terminal DNA fragments ending in several hundred bases of $(TTAGGG)_n$ (Stong, N., et al. (2014). "Subtelomeric CTCF and cohesin binding site organization using improved subtelomere assemblies and a novel annotation pipeline." Genome Res 24(6): 1039-1050), an HIV-1 entire genome-containing plasmid pEcoHIV-NL4-3-eLuc (gift from Dr Won-Bin Young at University of Pittsburgh) and genomic DNA isolated from human B-Lymphocyte cells NA12878 (Corriel Research Institute, NJ, USA).

The seed sequence of 20 nucleotides complementary to the 3'-5' strand of the target template DNA were designed via a gRNA design tool (Feng Lab CRISPR Design Web Tool at crispr.mit.edu). Each seed sequence was incorporated into the crRNA. Two crRNAs for the genomic sequences of DUF1220 domain (in BAC clone), 1 for the telomere repeat sequence $(TTAGGG)_n$ and 7 for subtelomeric sequences, along with the universal tracrRNA, were synthesized by GE Dharmacon. The fosmid and CH17-353B19 gRNAs were created by pre-incubating the tracrRNA (0.5 nmol) and corresponding crRNA (0.5 nmol) with 1×NEB Buffer 3 and 1×BSA at 4° C. for 30 min.

Three single guide RNAs (sgRNAs) containing seed sequence targeting HIV-1 structural gene regions (Gag, Pol and Env) were designed for efficiency and specificity using bioinformatics analysis tools. All the oligonucleotides for each target sequence (Table 3, Also see, Sequence Listing, which is incorporated by reference herein.) were synthesized in Alpha DNA (Montreal, Canada) and cloned into pKLVWG-sgRNA vector modified from pKLV-U6gRNA (BbsI)-PGKpuro2ABFP vector, a gift from Kosuke Yusa (Addgene plasmid #50946) (Koike-Yusa, H., et al. (2014). "Genome-wide recessive genetic screening in mammalian cells with a lentiviral CRISPR-guide RNA library." Nat Biotechnol 32(3): 267-273). The vector was digested with BbsI and treated with Antarctic Phosphatase, and the linearized vector was purified with the QIAquick® nucleotide removal kit (QIAGEN®). A pair of oligonucleotides for each targeting site was annealed, phosphorylated and ligated to the linearized vector. The sgRNA expression cassette was validated by sequencing with U6 sequencing primer in GENEWIZ®. The validated vector was used as template for PCR with forward T7-U6 and reverse sgRNA primer to generate T7 promoter-driven gRNA expression cassette. Then the sgRNA for each target was in vitro transcribed using MEGAshortscript™ T7 transcription kit (Life Technology®). The quality of HIV-1 sgRNAs was verified by electrophoresis in 5% denaturing polyacrylamide gel.

TABLE 3

Sequences for gRNAs.

| Loci | Loci number | Sequence 5'-3' | Type | SEQ ID NO. |
|---|---|---|---|---|
| DUF1220 | 1-12 | AAGUUCCUUUUAUGCAUUGG | gRNA | 2 |
| HIV plasmid | 1 | CACCGCAGGATATGTAACTGACAG | sgRNA | 3 |
|  | 2 | CACCGGCCAGATGAGAGAACCAAG | sgRNA | 4 |
|  | 3 | CACCGAGAGTAAGTCTCTCAAGCGG | sgRNA | 5 |
| Chr1q telomere | 1 | UUAGGGUUAGGGUUAGGGUU | gRNA | 6 |
| Chr1q subtelomere | 1 | CCCCUGUUGCCAGAGCCAGU | gRNA | 7 |
|  | 2 | GUAUUUAGUCAGAGGGCUAG | gRNA | 8 |
|  | 3 | AUACAGUAGGAUAACCGCAA | gRNA | 9 |
| Chr15q subtelomere | 1 | ACCUUGCUACCACGAGAGCA | gRNA | 10 |
|  | 2 | UCCAUUGGUUUAAUUAGGAA | gRNA | 11 |
| Chr11q subtelomere | 1 | GGUCCACCCUACAGAUGUGC | gRNA | 12 |
|  | 2 | AGAUCAGCAGCCACGUGUGC | gRNA | 13 |
| Chr12p subtelomere | 1 | ACCUUGCUACCACGAGAGCA | gRNA | 14 |
|  | 2 | UCCAUUGGUUUAAUUAGGAA | gRNA | 15 |
| Alu | 1 | UGUAAUCCCAGCACUUUGGG | gRNA | 16 |

Loci numbers designate the labels from left to right in FIGS. 3-5.

EXAMPLE 2—Cas9n Fluorescent Nick-Labeling of Fosmids, HIV-1 Plasmid and BAC Clone CH17-353B19

The gRNAs or sgRNAs (5 μM) were incubated with 600 ng of Cas9n D10A (PNA Bio Inc), 1×NEB Buffer 3 and 1×BSA (NEB) at 37° C. for 15 min. The DNA (500 ng) was added to the mixture and incubated at 37° C. for 60 min. The nicked DNA was then labeled with 4.12 units of DNA Taq Polymerase (NEB), 0.1 μM of ATTO-532 dUTP dAGC and 1× Thermopol Buffer (NEB) at 72° C. 60 min. The labeled fosmids and BACs were cut and linearized with 5 units of NotI enzyme (NEB) at 37° C. for 60 min. The labeled pecoHIV-NL4-3-eLuc plasmid (17,099 bp) was digested with 20 units of a unique restriction enzyme EcoRI (at 5744 bp) (NEB). NotI and EcoRI were inactivated at 65° C. for 20 min.

The distances were calculated between spots using ImageJ. The histogram of the label distributions were plotted in Excel. If the pattern matched the predicted pattern we considered the labels as true positives. Missing labels were used for the calculation of labeling efficiency and the extra labels were used for calculating the false positive percentage.

To establish the Cas9n fluorescent nick-labeling conditions and investigated the labeling efficiency with BAC clones, fosmids and plasmids as model systems. The Cas9n fluorescent nick-labeling of HLS DUF1220 triplets on a BAC clone were assessed (FIG. 3A). A single copy of HLS DUF1220 triplet spanned about 4.7 kb, and there were 12 copies on the BAC clone CH17-353B19. A gRNA probe was designed to target one unit of the triplets. Clearly, there were 12 copies detected on this 240 kb BAC clone and the distance between the each triplet measured 4.7 kb, which was in a good agreement with the clone sequence. The labeling efficiency of each locus was determined by evaluating 192 labeled BAC molecules, ranging from 87% to 98%. Interestingly, the middle copies (#6-8 labels from the left most one in FIG. 3A) were labeled at lower labeling efficiency.

The Cas9n fluorescent nick-labeling was very specific. The extra labels outside of the DUF domain were used to calculate the false positives in FIG. 3A. The spurious labels inside the DUF domain were harder to define because the DNA molecules inside the nanochannel were not static. Their slight movements and the limitation of optical resolution may cause inaccurate measurement of 4.7 kb repetitive sequences during the imaging time (200 ms). When all of the spurious spots inside and outside of the DUF domain were used, the false positive percentage is 0.6%.

Further, the Cas9n fluorescent nick-labeling method was applied to a plasmid containing the HIV-1 genome. Multiple sgRNAs were designed and tested to target HIV-1 structural region (Gag, Pol, Env) to determine the most effective gRNA that labels the HIV-1 genome. The sites were correctly labeled with the expected distances between each sgRNA (FIG. 3B). However, the labeling efficiencies at each site of 36%, 58% and 44% from the left most label respectively, suggesting that labeling efficiency may be sequence- or region-dependent. It could also be the difference in labeling efficiency of sgRNA versus gRNA. The labeling efficiencies of the gRNAs were much higher than those achieved using sgRNAs.

In a third model system, a fosmid containing a subtelomeric segment of human 1q ending in 100 bases of $(TTAGGG)_n$ was used to test the Cas9n fluorescent nick-labeling. Four guide RNA probes were designed to target the $(TTAGGG)_n$ tract and three distinct loci on the subtelomere. The labeling pattern matched very closely with the positions of the gRNA seed sequences in the 1q reference sequence (FIG. 3C). However, the labeling efficiency was relatively lower for the telomere with 30%, while the labeling efficiency of subtelomeric markers were 95%, 79% and 99% respectively from the left most left label on 1q (FIG. 3C). This might be due to non-Watson-Crick pairings of the hexameric repeats, the high G+C content or the secondary structure of guide RNA probes targeting the $(TTAGGG)_n$ repeat.

EXAMPLE 3—The Two Color Genome Mapping with Cas9n Fluorescent Nick Labeling and Sequence-Motif Labeling After nicking with Cas9n D10A as previously described in Example 2, the sample was digested with RNAseA (190 ng/μL, QIAGEN®) at 37° C. for 20 min. After digestion, the sample was labeled with ATTO 532-dATP, dTGC (100 nM) and 2.5 units of DNA Taq Polymerase (NEB) in the presence of 1× Thermopol Buffer (NEB) at 72° C. for 1 h. The sample was treated with 1 unit of SAP (USB® Products) and RNAseA (100 ng/μL) at 37° C. for 20 min and then 65° C. for 15 min. The nicks were repaired with 500 μM NAD+, 100 nM dNTPs and 20 kU of Taq DNA Ligase at 45° C. for 20 min. The sample was then treated with 6 mAU of QIAGEN Protease at 56° C. for 10 min and 70° C. for 15 min. The sample was dialyzed in TE on a 0.1 μm membrane (Millipore®) for 2 h. After dialysis, the sample was nicked with 10 units of Nt. BspQI (NEB) at 72° C. for 2 h. The nicked DNA was then labeled with 2.5 units of Taq DNA Polymerase (NEB), 0.1 μM ATTO-647 dUTP dAGC and 1× Thermopol Buffer (NEB) for 60 min at 72° C. The DNA backbone was stained with YOYO-1, and is shown in blue in all figures. The stained samples were loaded and imaged inside the nanochannels following the established protocol (See, Lam, E. T., et al. (2012). "Genome mapping on nanochannel arrays for structural variation analysis and sequence assembly." Nature Biotechnology 30(8): 771-776). The distances were calculated between spots using ImageJ. The histogram of the label distributions were plotted in Excel. If the pattern matched the predicted pattern we considered the labels as true positives. Missing labels were used for the calculation of labeling efficiency and the extra labels were used for calculating the false positive percentage.

The combination of Cas9n fluorescent nick-labeling with nicking endonuclease based sequence motif labeling was tested. This approach was designed to find wide applications in whole genome mapping of repetitive sequences as well as genotyping of structural variations and identification/mapping of viral integration sites. In FIG. 4A, the DUF1220 triplet repeats were first labeled with Cas9n fluorescent nick-labeling of red fluorescent nucleotides. These labeled DNA molecules were then globally nick-labeled with green nucleotides using Nt.BspQI to target the GCTCTTC motif. Twelve copies of DUF1220 triplets were detected spanning about 52 kb. Only the flanking regions of this 52 kb were shown to have the GCTCTTC motif, which can be mapped to reference genome to indicate the genomic locations of the DUF1220 triplet array. The histogram of the label distribution was shown in the bottom graph of FIG. 4A. Clearly, the combination of Cas9n fluorescent nick-labeling and nicking endonuclease sequence motif labeling, not only can detect the copy numbers of the DUF1220 triplets, but also can map the locations of the repeats.

The same approach was also applied to measure the telomere repeat length of a telomere-terminal fragment of chromosome 8q cloned in a fosmid. This fosmid carries 800 bp of the repetitive $(TTAGGG)_n$ sequence, which lacks motif nicking sites recognized by currently available nicking endonucleases and therefore cannot be labeled with current sequence-motif based methods. A gRNA specific for the telomere was designed. In FIG. 4B, the telomere was first labeled with Cas9n fluorescent nick-labeling of red fluorescent nucleotides. The labeled DNA molecules were then labeled with green nucleotides by Nt.BspQI nick-labeling to target the GCTCTTC motif. The telomere was correctly labeled on the end of the sequence. The length of this telomere region was determined by measuring the length of the red fluorophore region and the intensity of its fluorescence relative to known controls after imaging. Sequence motif labeling over extended subtelomere regions linked on single large DNA molecules to the Cas9n fluorescent nick-labeling $(TTAGGG)_n$ can be used to identify the specific subtelomere by comparison with genome-wide maps.

Cas9n fluorescent nick-labeling was used to create locus-specific and variant-specific barcodes. gRNAs were designed to create barcodes to distinguish individual subtelomeres linked on single molecules to $(TTAGGG)_n$ tracts (FIG. 5A, Chr 1q and Chr 11q) and to distinguish variant copies of highly similar subtelomeric segmental duplications (Chr 15q and Chr 12p) using the Cas9n sequence specific labeling methods. It has been suggested that the shortest telomere or a small subset of the shortest telomeres in a cell determines the onset of senescence, apoptosis or genome instability (Kaul, Z., et al. (2012). "Five dysfunctional telomeres predict onset of senescence in human cells." Embo Reports 13(1): 52-59; and Zou, Y., et al. (2004). "Does a sentinel or a subset of short telomeres determine replicative senescence?" Molecular Biology of the Cell 15(8): 3709-3718), the ability to systematically measure individual dysfunctionally short $(TTAGGG)_n$ tracts (rather than average telomere tract lengths in a sample as is typically measured currently) would provide important new high-resolution information on specific telomere functional status and identity at the single-molecule level. On the telomeric fosmids from Chr 15q and Chr 12p (FIG. 5A), Cas9n-gRNA directed nicks at two loci in a segmentally duplicated subtelomere region containing the WASH gene family (See, Linardopoulou, E. V., et al. (2007). "Human subtelomeric WASH genes encode a new subclass of the WASP family." PLoS Genet 3(12): e237) were labeled in red. The same pair of gRNAs generated signals separated by 5.87 kb on the 15q fosmid and 7.5 kb on Chr 12p fosmid, as predicted by the reference sequences of these two highly similar but structurally non-identical regions. The patterns generated by three target-specific gRNAs on Chr1q and two gRNAs on 11q were unique, easily distinguishable from each other and from both of the WASH gene-related patterns, and corresponded exactly to what was expected from their respective reference sequences. These experiments indicate that specific gRNAs were pooled to generate multiple specific nicks that, when labeled, can create custom barcodes predicted precisely by the respective reference sequences.

FIG. 5B shows the results of experiments combining the Cas9n fluorescent nick-labeling and nicking endonuclease sequence motif labeling to map Alu elements in the human genome. A gRNA was designed to target 280 000 Alu sites out of one million copies. Typical genomic DNA molecules were imaged and shown in FIG. 5B. One 180 kb molecule displayed dense Alu elements with only two GCTCTTC motifs. Another DNA molecule showed dense Alu elements with two GCTCTTC motifs. The combined information can be used to map the DNA molecules to the reference genome and profile the distribution of Alu elements on the whole genome scale.

All publications cited in this specification are incorporated herein by reference in their entireties, as are U.S. Provisional Patent Application No. 62/410,322, filed Oct. 19, 2016, and U.S. Provisional Patent Application No. 62/410,324, filed Oct. 19, 2016. Similarly, the Sequence Listing filed herewith is hereby incorporated by reference. While the invention has been described with reference to particularly preferred embodiments, it will be appreciated that modifications can be made without departing from the spirit of the invention. Such modifications are intended to fall within the scope of the appended claims.

The invention claimed is:

1. A method of labeling a nucleic acid sequence comprising:
   a) contacting genomic DNA with a guide RNA having a seed sequence which is complementary to a target sequence in the genomic DNA and with Cas9 nickase to produce a nick in the genomic DNA at a specific location adjacent to the target sequence; and contacting the nicked DNA with a polymerase and fluorescently labeled nucleotide, wherein the fluorescently labeled nucleotide is incorporated into the nicked genomic DNA at the specific location; and
   b) contacting the nicked genomic DNA with a motif-specific nicking endonuclease thereby producing a second nick in the nicked genomic DNA at a motif sequence; and contacting the nicked genomic DNA with a polymerase and second fluorescently labeled nucleotide of the same color or different color, wherein the second fluorescently labeled nucleotide is incorporated into the nicked genomic DNA at the motif sequence location;
   wherein nick-labeled DNA is produced; and
   wherein the nick-labeled DNA is detected via fluorescent label.

2. The method of claim 1, wherein step b) is performed before step a).

3. The method of claim 1, wherein a pattern of fluorescence provided by the Cas9 nickase is used as a barcode to identify the location or identity of the genomic DNA.

4. The method of claim 1, wherein a pattern of fluorescence provided by the motif-specific nicking endonuclease is used as a barcode to identify the location or identity of the genomic DNA.

5. The method of claim 1, wherein a pattern of fluorescence provided by the Cas9 nickase and the motif-specific nicking endonuclease is used as a barcode to identify the location or identity of the genomic DNA.

6. The method according to claim 1, wherein the guide RNA comprises a crRNA and a tracrRNA.

7. The method according to claim 1, wherein the guide RNA is a single gRNA sequence.

8. The method according to claim 1, where the guide RNA and the Cas9 nickase are contacted with each other to form a complex, prior to contacting with the genomic DNA.

9. The method according to claim 1, wherein the Cas9 nickase is Cas9 D10A or H840A.

10. The method according to claim 1, wherein the genomic DNA is contacted with multiple guide RNAs, each guide RNA having a seed sequence complementary to a different target sequence in the genomic DNA, wherein each target nucleic acid sequence is detected via the same or different fluorescent label, thus providing a barcode of a portion of the genomic DNA.

11. The method of claim 1, wherein the guide RNA targets a repeated sequence.

12. The method according to claim 1, wherein the target sequence is a viral nucleic acid sequence.

13. The method according to claim 1, wherein the target sequence is a sequence adjacent to a translocation breakpoint.

14. The method according to claim 1, further comprising repairing the nick-labeled DNA with a ligase.

15. The method according to claim 1, further comprising imaging the nick-labeled DNA in a nanochannel.

16. The method according to claim 15, comprising transporting the nick-labeled DNA into a nanochannel and maintaining the DNA in elongated form in the nanochannel.

17. The method according to claim 1, further comprising staining the DNA backbone.

18. The method according to claim 1, wherein the motif-specific nicking endonuclease is Nt.BspQI.

19. The method according to claim 1, wherein the target sequence is present in more than one location in the genomic DNA.

20. The method according to claim 1, further comprising one or more of:
   i. treating the DNA with RNAse;
   ii. treating the DNA with protease;
   iii. Removing labeled free nucleotides;
   iv. Linearizing the DNA; and
   v. Fragmenting the DNA.

* * * * *